(12) United States Patent
Berens et al.

(10) Patent No.: US 9,108,988 B2
(45) Date of Patent: Aug. 18, 2015

(54) METHOD OF PURIFYING ORGANIC DIPHOSPHITE COMPOUNDS

(71) Applicant: BASF SE, Ludwigshafen (DE)

(72) Inventors: Ulrich Berens, Binzen (DE); Holger Ganz, Ludwigshafen (DE); Franz Niklaus Windlin, Heidelberg (DE); Walid Al-Akhdar, Oberwil (CH)

(73) Assignee: BASF SE, Ludwigshafen (DE)

( * ) Notice: Subject to any disclaimer, the term of this patent is extended or adjusted under 35 U.S.C. 154(b) by 64 days.

(21) Appl. No.: 13/731,725

(22) Filed: Dec. 31, 2012

(65) Prior Publication Data
US 2013/0225849 A1   Aug. 29, 2013

Related U.S. Application Data

(60) Provisional application No. 61/581,658, filed on Dec. 30, 2011.

(51) Int. Cl.
| C07F 9/547 | (2006.01) |
| C07F 9/02 | (2006.01) |
| C07F 9/6574 | (2006.01) |

(52) U.S. Cl.
CPC ............. *C07F 9/025* (2013.01); *C07F 9/65746* (2013.01)

(58) Field of Classification Search
USPC .................................................. 558/146, 147
See application file for complete search history.

(56) References Cited

U.S. PATENT DOCUMENTS

| 4,668,651 A | 5/1987 | Billig et al. | |
| 4,748,261 A | 5/1988 | Billig et al. | |
| 4,769,498 A | 9/1988 | Billig et al. | |
| 4,835,299 A | 5/1989 | Maher et al. | |
| 4,885,401 A | 12/1989 | Billig et al. | |
| 5,235,113 A | 8/1993 | Sato et al. | |
| 5,312,996 A | 5/1994 | Packett | |
| 5,391,801 A | 2/1995 | Sato et al. | |
| 5,616,767 A * | 4/1997 | Enlow et al. | 558/92 |
| 5,663,403 A | 9/1997 | Sato et al. | |
| 5,728,861 A | 3/1998 | Sato et al. | |
| 6,127,567 A | 10/2000 | Garner et al. | |
| 6,172,267 B1 | 1/2001 | Urata et al. | |
| 8,796,481 B2 | 8/2014 | Berens et al. | |
| 2003/0100787 A1 | 5/2003 | Akbarali et al. | |
| 2004/0073035 A1 | 4/2004 | Maase et al. | |
| 2007/0112219 A1 | 5/2007 | Ortmann et al. | |
| 2008/0083606 A1 | 4/2008 | Volland et al. | |
| 2009/0247790 A1 | 10/2009 | Miller | |
| 2011/0201837 A1 | 8/2011 | Fridag et al. | |
| 2011/0207966 A1 | 8/2011 | Fridag et al. | |
| 2013/0172596 A1 | 7/2013 | Berens et al. | |
| 2014/0288322 A1 | 9/2014 | Miller et al. | |

FOREIGN PATENT DOCUMENTS

| CN | 101684130 A | 3/2010 |
| DE | 10360771 A1 | 7/2005 |
| EP | 0214622 A2 | 3/1987 |
| EP | 0285136 A2 | 10/1988 |
| WO | WO-03062171 A2 | 7/2003 |
| WO | WO-03062251 A1 | 7/2003 |
| WO | WO-2009120210 A1 | 10/2009 |
| WO | WO-2010042313 A1 | 4/2010 |
| WO | WO-2010052090 A1 | 5/2010 |

(Continued)

OTHER PUBLICATIONS

Christiansen, A., et al., "Heteroatom-Substituted Secondary Phosphine Oxides (HASPOs) as Decomposition Products and Preligands in Rhodium-Catalysed", Chemistry & European Journal, vol. 17, (2011), pp. 2120-2129.

International Search Report for PCT/EP2012/077018, dated Apr. 12, 2013.

Junge, K., et al., "Synthesis and catalytic application of novel binaphthyl-derived phosphorous ligands", ARKIVOC, No. 5, (2007), XP055057476, DOI: 10.3998/ark.5550190.0008.506.

Van Rooy, A., et al., "Bulky Diphosphite-Modified Rhodium Catalysts: Hydroformylation and Characterization", Organometallics, vol. 15, No. 2, (1996), pp. 835-847.

Yan, M., et al., "Asymmetric hydrocyanation of olefins catalyzed by chiral diphosphite-nickel complexes", Tetrahedron Asymmetry, vol. 11, No. 4, (2000), pp. 845-849.

(Continued)

*Primary Examiner* — Sudhakar Katakam
*Assistant Examiner* — Pancham Bakshi
(74) *Attorney, Agent, or Firm* — Drinker Biddle & Reath LLP

(57) ABSTRACT

A method of purifying an organic diphosphite of general formula (I)

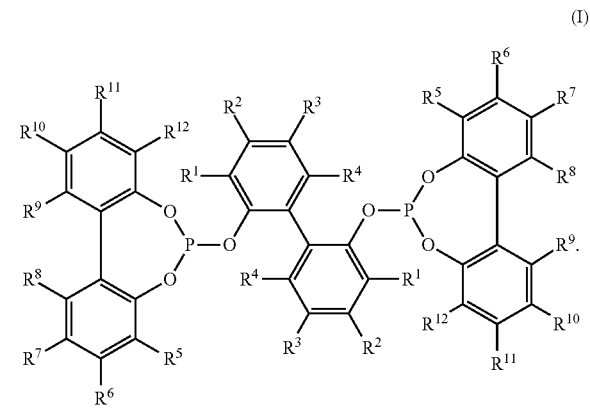

The method comprises providing a crude organic diphosphite of general formula (I) that is at least partly dissolved in a first solvent (L1), wherein (L1) is selected from the group consisting of alkylbenzenes, aryl alkyl ethers, chlorobenzene, and mixtures thereof, and precipitating by admixing with a second solvent (L2) selected from the group consisting of linear $C_1$-$C_4$-alkanols, ethylene glycol di($C_1$-$C_4$-alkyl) ethers, and mixtures thereof, and separating off the precipitated organic diphosphite from the solvents.

42 Claims, 2 Drawing Sheets

(56) References Cited

FOREIGN PATENT DOCUMENTS

| WO | WO-2010052091 A1 | 5/2010 |
| WO | WO2013/066712 | 5/2013 |

OTHER PUBLICATIONS

Yan, M., et al., "Enantioselective conjugate addition of diethyzinc to enones catalyzed by a copper complex of chiral aryl diphosphite", Chem. Commun., No. 1, (1999), pp. 11-12.

* cited by examiner

METHOD OF PURIFYING ORGANIC DIPHOSPHITE COMPOUNDS

RELATED APPLICATIONS

This application claims benefit (under 35 USC 119(e)) of U.S. Provisional Application Ser. No. 61/581,658, filed Dec. 30, 2011, which is incorporated herein by reference in its entirety.

BACKGROUND OF THE INVENTION

The present invention relates to a method of purifying organic diphosphite compounds.

Organic diphosphite compounds have found extremely widespread use, for example as chelating ligands in homogeneous catalysis, and also as flame retardants, UV stabilizers, etc. Particular rhodium complexes with organic diphosphite compounds have been found to be useful as catalysts for the hydroformylation of olefins since they firstly have a high catalytic activity and secondly lead predominantly to linear aldehydes which are preferred for many applications. Organic diphosphite compounds are also suitable as ligands for transition metal complex catalysts for hydrocyanation, hydrogenation, carbonylation, hydroacylation, hydroamidation, hydroesterification, hydrosilylation, hydroboration, alcoholysis, isomerization, allylic alkylation or hydroalkylation.

Such diphosphite compounds, their preparation and their use as ligands in a hydroformylation process are described, for example, in EP 0 214 622 A2, U.S. Pat. No. 4,668,651, U.S. Pat. No. 4,748,261, U.S. Pat. No. 4,769,498, U.S. Pat. No. 4,885,401, U.S. Pat. No. 5,235,113, U.S. Pat. No. 5,391,801, U.S. Pat. No. 5,663,403, U.S. Pat. No. 5,728,861 and U.S. Pat. No. 6,172,267. The use in a hydrocyanation process is also described in U.S. Pat. No. 6,127,567.

Organic diphosphites of the general formula (A) are usually prepared by a process comprising the following steps:

a) reaction of a compound of the formula (A1) (=first aromatic diol) with phosphorus trichloride to give the phosphomonochloridite (A2)

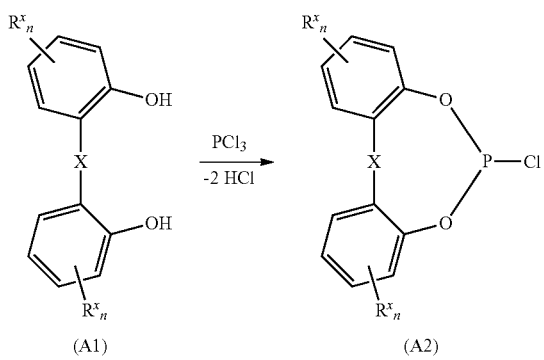

(A1)        (A2)

b) reaction of the phosphomonochloridite (A2) with a compound of the formula (A3) (=second aromatic diol) to give the chelating diphosphite (A)

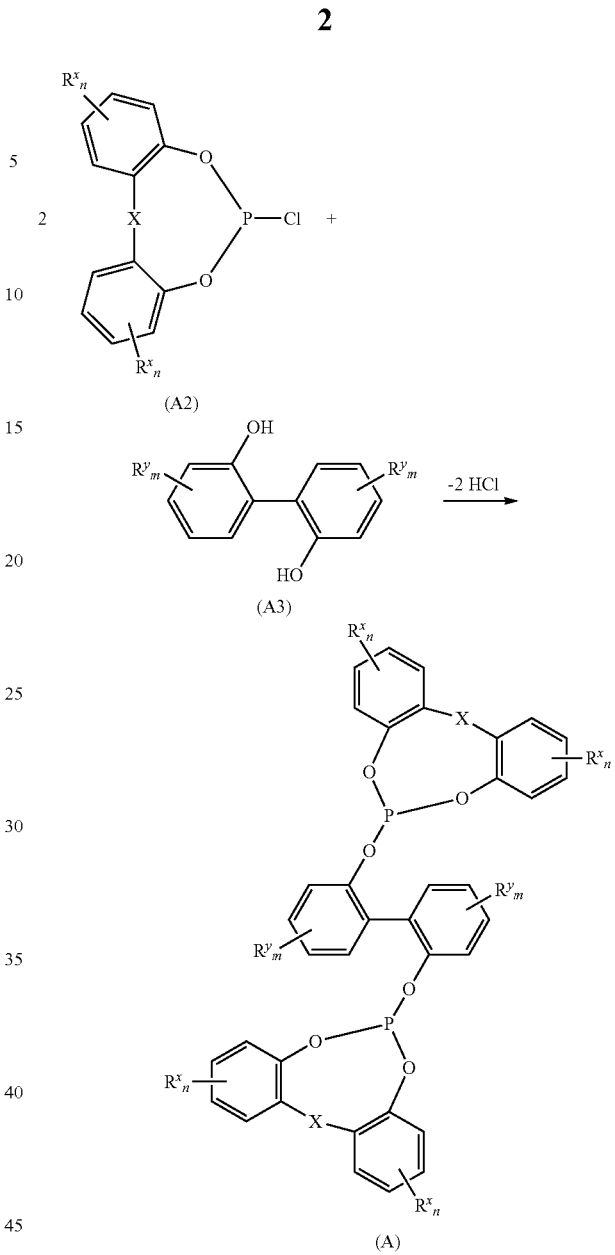

The groups derived from the first aromatic diol (A1) in the organic diphosphites will hereinafter also be referred to as "side wings".

The preparation of diphosphites in which at least one of the phosphorus atoms is not part of a heterocycle is carried out analogously by, in step a), reacting $PCl_3$ with two molar equivalents of an appropriate monoalcohol instead of one molar equivalent of the first aromatic diol (A1). To prepare diphosphites in which the two phosphorus atoms are bridged by other groups, other diols can be used instead of the backbone diol (A3).

One possible way of removing the hydrogen halides liberated in the condensation reaction is the use of an at least stoichiometric amount of base, with nitrogen bases frequently being used. However, the removal of the resulting acid salts is frequently difficult and the salts can often not be recycled sensibly and have to be disposed of, which is associated with additional costs.

WO 2003/062171 and WO 2003/062251 describe a method of separating acids from reaction mixtures by means of an auxiliary base which with the acid forms a salt which is liquid at temperatures at which the desired product is not significantly decomposed during removal of the liquid salt and the salt of the auxiliary base forms two immiscible liquid phases with the desired product or the solution of the desired product in a suitable solvent. In other words, the acid salts of the auxiliary base behave like ionic liquids which are essentially immiscible with the actual reaction solvent. Preferred auxiliary bases of this type are 1-methylimidazole, 1-n-butylimidazole, 2-methylpyridine and 2-ethylpyridine. The methods described in WO 2003/062171 and WO 2003/062251 are suitable, inter alia, for phosphorylation reactions such as the above-described synthesis of phosphomonochloridites and the reaction thereof with an aromatic diol to give a diphosphite compound.

In general, organic diphosphite compounds have to be subjected after the synthesis to a purification in order to remove interfering impurities before use in a catalysis process.

Potential impurities can be independent of the synthesis process used, e.g. decomposition or other subsequent products typical of this class of material or be formed during the course of the synthesis. Problematical impurities are, firstly, impurities which can form complexes with transition metals such as rhodium, e.g. acetonitrile, and thus have a potential influence on use of the diphosphite compounds as catalysts. These include, for example, secondary organophosphites which will be discussed in more detail below. Also problematical are impurities which make the use of expensive apparatuses necessary, e.g. corrosive halides, especially chloride. Chloride ions are also known catalyst poisons for rhodium complex catalysts.

Adverse effects of impurities in the organic diphosphite compounds can affect the process itself in which they are used as ligands. Thus, impurities which act as catalyst poisons and/or lead to decomposition of the catalyst have an adverse effect on the catalyst operating life, which can over time lead to operational malfunctions. This applies, in particular, to the use of the organic diphosphite compounds in a continuous process in which impurities can accumulate. Adverse effects of these impurities can also affect the desired products produced in the respective process by having adverse effects on product properties, e.g. the storage behavior, the handleability, the odor, the color, the keeping qualities, etc.

The substantially complete removal of impurities is therefore a critical prerequisite for the organic diphosphite compound to be able to be used successfully in an industrial process.

Typical impurities from the synthesis of organic diphosphite compounds are residues of the base (generally an organic nitrogen-comprising compound, e.g. an amine) used for scavenging the hydrogen halide (generally HCl) liberated in the reaction, the acid salts of this base and possibly also residues of the hydrogen halide. Typical impurities from the synthesis also include catalysts which are intended to accelerate the reaction of the phosphorus trihalide with the aromatic alcohols. Even when, as described in WO 2003/062171 and WO 2003/062251, a compound whose acid salts behave like ionic liquids which are essentially immiscible with the solution of the organic diphosphite compound in an appropriate organic solvent, e.g. toluene, and can thus easily be separated off by phase separation is used as base, purification of the crude ligand solution is generally nevertheless absolutely necessary.

DE 103 60 771A1 teaches carrying out the reaction of phosphorus halides with organic compounds which have at least one OH group in the presence of a basic ion-exchange resin.

WO 2009/120210 and the US patent 2009/0247790 of the same priority date describe a process for preparing phosphomonochloridites which can be used as intermediate for introducing the side wings in the preparation of chelating diphosphite compounds. According to these documents, the reaction of $PCl_3$ with an aromatic diol occurs in a solution comprising less than 5 mol % of a nitrogen base, based on mol of aromatic diol, with HCl formed being driven from the reaction solution and the reaction being carried out under essentially isothermal conditions. However, this is associated with the disadvantage that hydrogen chloride gas discharged as offgas stream has to be isolated in a separate scrubber and disposed of. In addition, solvent is generally also discharged with the offgas stream. However, in order to avoid emissions, the solvent entrained in the offgas has to be removed, which can be effected, for example, by incineration and requires an additional outlay.

WO 2010/042313 describes a process for preparing organic diphosphites, in which the reaction of $PCl_3$ with the first aromatic diol forming the side wings is carried out in the presence of the second aromatic diol which bridges the two phosphorus atoms and the reactants are brought into contact with one another as a slurry in an organic solvent and the slurry comprises less than 5 mol % of a nitrogen base, based on mol of first diol, and the organic solvent has only a slight solvent capacity for HCl. This procedure leads to a reduction in the amount of acid salts formed by scavenging of the HCl by means of base in the condensation reaction.

Once again, the hydrogen chloride gas discharged as offgas stream has to be isolated and disposed of.

WO 2010/052090 and WO 2010/052091 describe processes for preparing 6-chlorodibenzo[d,f][1,3,2]dioxaphosphepin, which can be used as intermediate for introduction of the side wings in the preparation of chelating diphosphite compounds. In these processes, 2,2'-dihydroxybiphenyl suspended in an inert solvent is added to an excess of phosphorus trichloride under inert gas in a reactor with stirring and the gases formed are discharged from the reaction mixture. Thus, an addition of base in the reaction can be dispensed with. The hydrogen chloride discharged as offgas stream has to be collected, for which, according to the teachings of this document, a separate scrubber is used. However, to avoid emissions, the solvent entrained in the offgas has to be removed, which can, for example, be carried out by incineration and requires an additional outlay.

Further impurities which can be comprised in the solution of the crude organic diphosphite are the monoxide (B1) and dioxide (B2) thereof or the hemiligand (B3) formed by incomplete reaction of the backbone.

(B1)

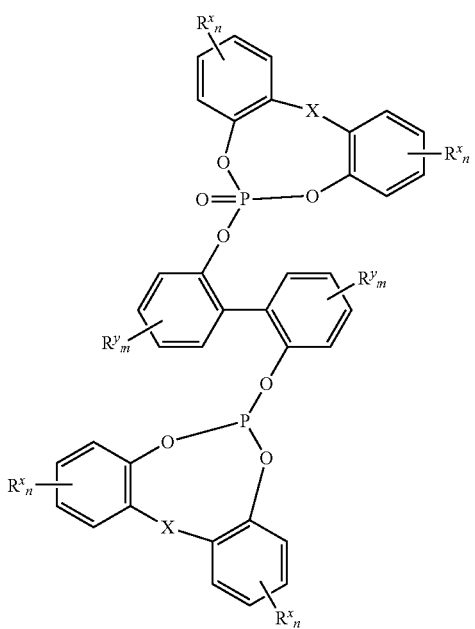

(B2)

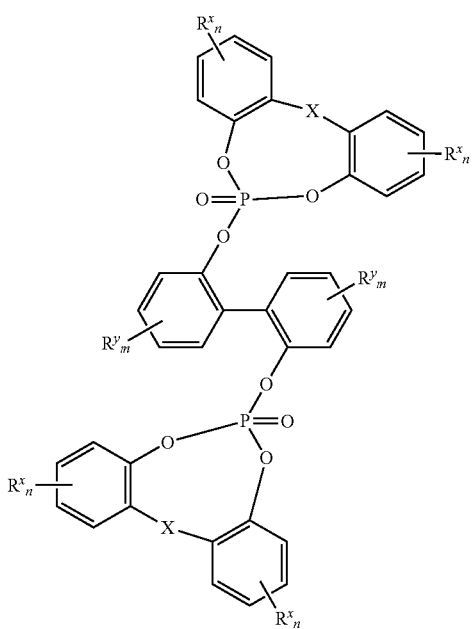

(B3)

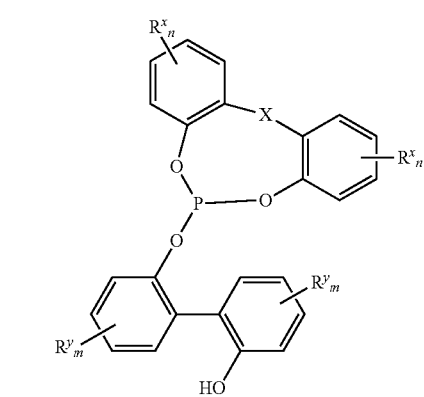

In Chem. Eur. J. 2011, 17, 2120, A. Christiansen et al. describe the formation of heteroatom-substituted secondary phosphine oxides as decomposition products and preligands in rhodium-catalyzed hydroformylation. The corresponding secondary organophosphites (C1) formed in the hydrolysis of tertiary phosphites represent a problematic impurity in the crude chelating diphosphite solution since they act as acid and decompose the acid-labile chelating diphosphites over the course of time. In addition, the compounds (C1) act as catalyst poison by complexing transition metals such as rhodium and when they accumulate in the reactor over prolonged periods of time can lead to deposition of the transition metal from the homogeneous reaction solutions and lead to rhodium losses. Since the transition metal is then no longer available for catalysis, operational malfunctions are the result. Especially in hydroformylation, the compounds (C1) can condense with the aldehydes formed to give •-hydroxyphosphonates (C2). Both the compounds (C1) and the compounds (C2) lead, as a result of their acidity, to hydrolytic decomposition of the chelating phosphite ligands. This process also proceeds autocatalytically since further (C1) is formed in the hydrolysis of the chelating phosphite ligands.

(C1)

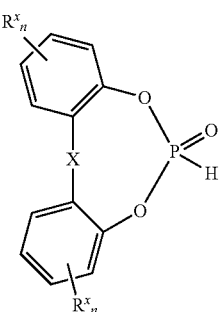

(C2)

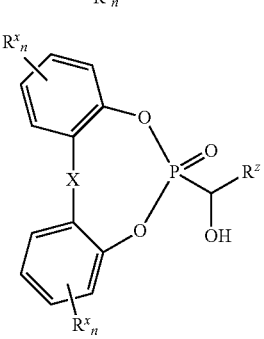

EP 0 285 136 A2 describes a method of purifying tertiary organophosphites by separating off secondary organophosphites, especially secondary organophosphites having a tetracoordinated phosphorus atom as in C1. This document refers to the problem that secondary organophosphites generally cannot be separated off from tertiary organophosphites by simple recrystallization since these compounds frequently cocrystallize. EP 0 285 136 A2 therefore teaches adding water and a Lewis base which selectively converts secondary organophosphites into salts of primary organophosphites to a solution of the secondary and tertiary organophosphites in an organic solvent so that the salts of primary organophosphites can then be separated off from the tertiary organophosphites. Suitable Lewis bases are NaOH and tertiary amines, e.g. triethylamine.

CN 101684130A describes a process for preparing chelating phosphites, in which
a.) the phosphomonochloridite forming the side wings is dissolved in dichloromethane,
b.) the aromatic diol which bridges the two phosphorus atoms is dissolved in triethylamine or a triethylamine/dichloromethane mixture,
c.) the solutions from a.) and b.) are mixed and reacted at from −40° C. to 20° C.,
d.) the resulting solution is stirred at from 20 to 30° C. for from 10 to 20 hours and
e.) deionized water is added to the solution from step d.), the mixture is stirred, the phases are allowed to separate, with the lower organic phase comprising the phosphite product.

The chelating phosphites obtained in this way are characterized, inter alia, by a chloride ion content of less than 0.01% by weight (100 ppm).

US 2003/0100787 describes a process for preparing sterically hindered triaryl monophosphites, but a possible use for preparing diphosphites is not described. According to the preparative examples, the synthesis of these monophosphites is carried out by reaction of substituted phenols with $PCl_3$ in the presence of pyridine and methylene chloride as solvent. After the reaction, the methylene chloride is distilled off and the monophosphite is induced to crystallize by addition of isopropanol.

Studies on the rhodium-catalyzed hydroformylation of 1-octene and styrene using bulky chelating phosphite ligands are described in Organometallics 1996, 15(2), 835-847. In the preparation of ligand (9) (6,6'-[[3,3',5,5'-tetrakis(1,1-dimethylethyl)-[1,1'-biphenyl]-2,2'-diyl]bis(oxy)]bisdibenzo[d,f][1,3,2]dioxaphosphepin), it is stated that the ligand obtained after taking off the solvent and excess pyridine is firstly induced to crystallize by addition of acetonitrile and is then recrystallized from a toluene/acetonitrile mixture.

U.S. Pat. No. 5,312,996 describes, in column 18, line 60 ff., a ligand synthesis by reaction of 1,1'-biphenyl-3,3'-di-tert-butyl-5,5'-di-tert-butoxy-2,2'-diol with biphenol chloridite in toluene and in the presence of pyridine. The pyridinium chloride formed is filtered off from the reaction product obtained. The resulting solution is evaporated on a rotary evaporator until it has a syrupy consistency and the diphosphite obtained is then precipitated by addition of acetonitrile. The solid obtained is filtered off, washed with acetonitrile and dried.

It is an object of the present invention to provide a simple and effective method of purifying organic diphosphite compounds. The diphosphite compound obtained should have a purity which makes it possible for the diphosphite compound to be used as ligand in a continuous industrial process. Contamination with compounds from the production process, e.g. acetonitrile, which have an adverse effect on use of the organic diphosphites as ligands for catalysts for homogeneous catalysis should be avoided. In particular, the content of secondary organophosphites should also be very low. The organic diphosphite compound obtained should preferably be obtained in a solid form with good use properties. Such forms include, for example, crystals which are large enough for them to be able to be separated off readily by filtration and/or have only a small level of occlusions of solvent (occluded solvent) with impurities comprised therein.

It has now surprisingly been found that a crude organic diphosphite which is at least partly dissolved in an organic solvent can be effectively freed of the abovementioned impurities by precipitation by means of a precipitant (i.e. a solvent in which it is sparingly soluble).

SUMMARY OF THE INVENTION

The invention firstly provides a method of purifying organic diphosphites of the general formula (I)

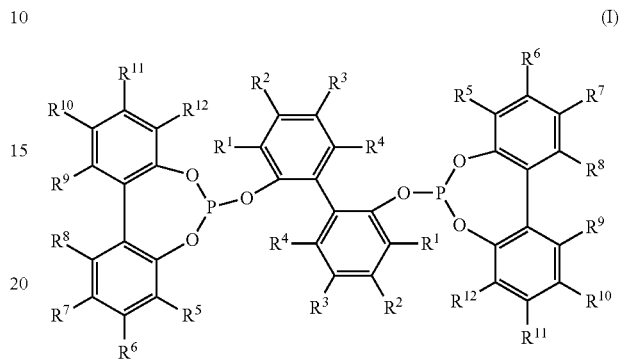

where
$R^1$, $R^2$, $R^3$ and $R^4$ are each, independently of one another, hydrogen, $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, chlorine, bromine, hydroxy, formyl, acyl or alkoxycarbonyl,
  where two adjacent radicals $R^1$ to $R^4$ together with the carbon atoms of the benzene ring to which they are bound can also form a fused ring system with a further benzene ring,
$R^5$, $R^6$, $R^7$, $R^8$, $R^9$, $R^{10}$, $R^{11}$ and $R^{12}$ are each, independently of one another, hydrogen, $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, chlorine, formyl, acyl or alkoxycarbonyl,
  where two adjacent radicals $R^5$ to $R^{12}$ together with the carbon atoms of the benzene ring to which they are bound can also form a fused ring system with a further benzene ring,
  where $C_1$-$C_{12}$-alkyl and $C_1$-$C_{12}$-alkoxy can each be unsubstituted or substituted by one or more identical or different radicals $R^a$ selected from among $C_3$-$C_{12}$-cycloalkyl, $C_3$-$C_{12}$-heterocycloalkyl, $C_6$-$C_{20}$-aryl, fluorine, chlorine, cyano, formyl, acyl and alkoxycarbonyl,
  where $C_3$-$C_{12}$-cycloalkyl and $C_3$-$C_{12}$-heterocycloalkyl can each be unsubstituted or substituted by one or more identical or different radicals $R^b$ selected from among $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, fluorine, chlorine, bromine, cyano, formyl, acyl and alkoxycarbonyl,
  where $C_6$-$C_{20}$-aryl and can in each case be unsubstituted or substituted by one or more identical or different radicals $R^c$ selected from among $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, fluorine, chlorine, bromine, cyano, formyl, acyl and alkoxycarbonyl,
wherein a crude organic diphosphite of the general formula (I) which is at least partly dissolved in a first solvent (L1) selected from among alkylbenzenes, aryl alkyl ethers, chlorobenzene and mixtures thereof is precipitated by admixing with a second solvent (L2) selected from among linear $C_1$-$C_4$-alkanols, ethylene glycol di($C_1$-$C_4$-alkyl)ethers and mixtures thereof.

Preference is given to a method of purifying organic diphosphites of the general formula (I)

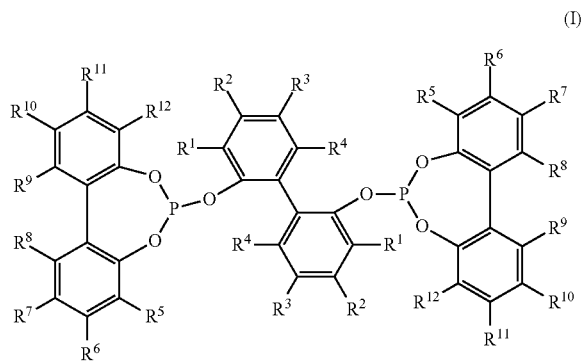

where
R¹, R², R³ and R⁴ are each, independently of one another, hydrogen, unsubstituted straight-chain or branched $C_1$-$C_6$-alkyl, unsubstituted straight-chain or branched $C_1$-$C_6$-alkoxy, $C_6$-$C_{10}$-aryl, chlorine, formyl, acyl or ($C_1$-$C_6$-alkoxy)carbonyl,
where two adjacent radicals R¹ to R⁴ together with the carbon atoms of the benzene ring to which they are bound can also form a fused ring system with a further benzene ring,
R⁵, R⁶, R⁷, R⁸, R⁹, R¹⁰, R¹¹ and R¹² are each, independently of one another, hydrogen, unsubstituted straight-chain or branched $C_1$-$C_6$-alkyl, unsubstituted straight-chain or branched $C_1$-$C_6$-alkoxy, $C_6$-$C_{10}$-aryl, chlorine, formyl, acyl or ($C_1$-$C_6$-alkoxy)carbonyl,
where two adjacent radicals R⁵ to R¹² together with the carbon atoms of the benzene ring to which they are bound can also form a fused ring system with a further benzene ring,
wherein a crude organic diphosphite of the general formula (I) which is at least partly dissolved in a first solvent (L1) selected from among alkylbenzenes, aryl alkyl ethers, chlorobenzene and mixtures thereof is precipitated by admixing with a second solvent (L2) selected from among linear $C_1$-$C_4$-alkanols, ethylene glycol di($C_1$-$C_4$-alkyl)ethers and mixtures thereof.

In a first variant of the method, precipitation of the crude organic diphosphite is preferably effected by crystallization.
A first variant is a method in which
a) a solution comprising the crude organic diphosphite of the general formula (I) and the first solvent (L1) is provided,
b1) the organic diphosphite is partly crystallized out by distilling off part of the first solvent (L1) and, to complete the crystallization, the second solvent (L2) is added and
c) the crystallized organic disphosphite is separated off from the liquid phase.
The organic diphosphite is preferably partly crystallized out hot in step b1) by distilling off part of the first solvent (L1).
A second variant is a method in which
a) a solution comprising the crude organic diphosphite of the general formula (I) and the first solvent (L1) is provided,
b2) the solution provided in step a) is added to the second solvent (L2), with the organic diphosphite at least partly precipitating, and
c) the precipitated organic diphosphite is separated off from the liquid phase.
In a preferred embodiment, the solution provided in step a) is added hot to the second solvent (L2) in step b2).
In a preferred embodiment, the organic diphosphite obtained in step c) is worked up by subjecting it to washing with a liquid washing medium (step d)).

The invention further provides for the use of a transition metal catalyst comprising, as a ligand, at least one organic diphosphite obtained by a purification method as defined above and below for hydroformylation, hydrocyanation or hydrogenation.

A BRIEF DESCRIPTION OF THE FIGURES

DESCRIPTION OF THE INVENTION

Figure 1:
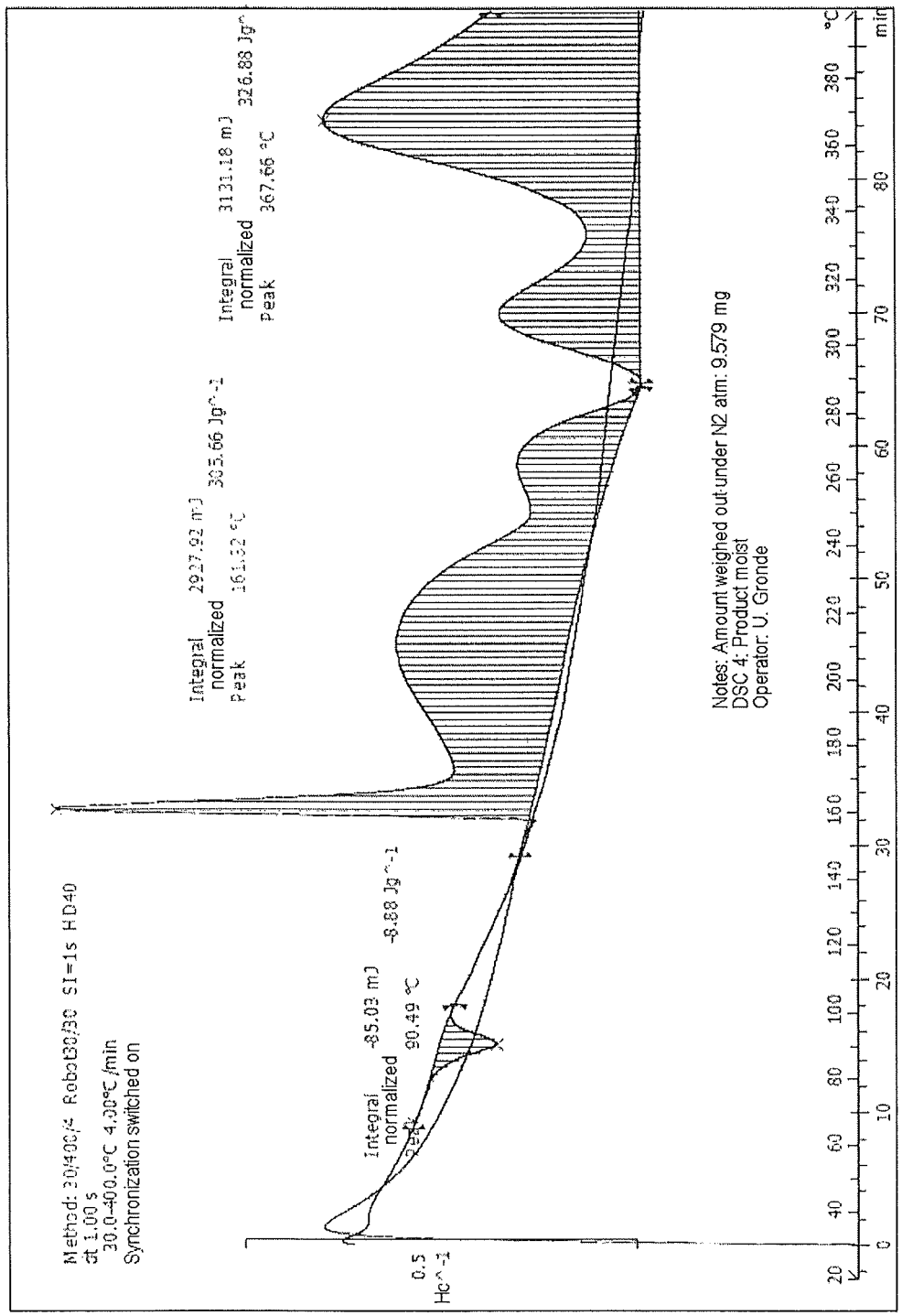
FIG. 1 shows the differential scanning calorimetry (DSC) measurement of the methanol-moist filter cake of I obtained in example 4 which has been sucked dry as far as possible.

The method of the invention has the following advantages:
The method is simple and effective.
The organic diphosphites obtained are sufficiently pure for them to be used as
The purification method of the invention makes it possible, in particular, to achieve a significant reduction in the content of secondary organophosphites.
The diphosphite compounds obtained have no detectable amounts of diols of the general formula (Aii)

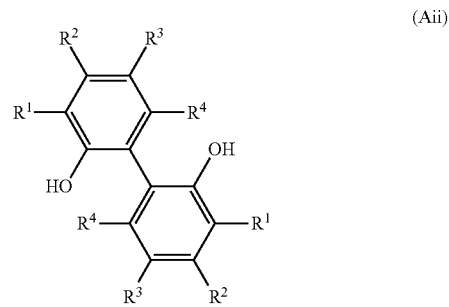

which form the backbone of the organic diphosphites of the general formula (I). The diols (Aii) are undesirable because of their relatively high acidity and the subsequent associated risk of destruction of the organic diphosphites.

The diphosphite compounds obtained have only low contents of halide ions, especially chloride ions.

The diphosphite compounds obtained have, in particular, no detectable amounts of secondary phosphites C1 or tertiary monophosphites D1 and/or D2

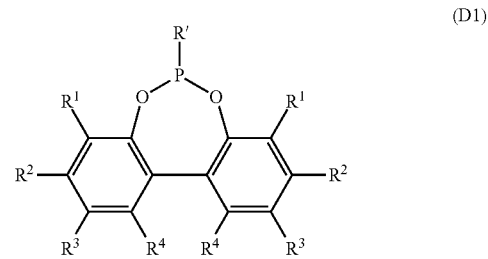

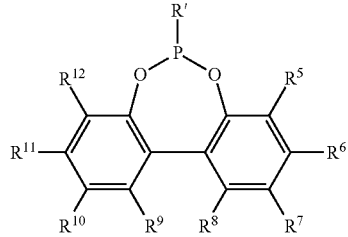

(D2)

where R' is alkoxy, preferably $C_1$-$C_4$-alkoxy, in particular methoxy. This is surprisingly also the case when a C1-C4-alkanol, in particular methanol, is used as second solvent (L2).

The second variant of the method of the invention (comprising steps a), b2) and c)) is particularly preferred. It additionally has the following advantages:

The organic diphosphite is obtained in the form of fine, very readily filterable crystals.

The organic diphosphite occludes only small amounts of the mother liqor, i.e. solvents L1, L2 and impurities dissolved therein. Merely to avoid misunderstandings, it is pointed out that occlusions of solvent are not solvates in which the solvent is incorporated into the crystal lattice and which form a different crystal than the corresponding nonsolvates.

Further purification by recrystallization is not necessary.

The product obtained by the method of the invention is a free-flowing powder which does not tend to cake during storage and retains its free-flowing nature over a prolonged period of time.

For the purposes of the invention, a crude diphosphite is a composition of the organic diphosphite of the general formula (I) before purification, as is generally formed in the synthesis thereof and comprises one or more impurities, e.g. by-products, starting materials, catalysts and/or other auxiliaries for the synthesis.

When the organic diphosphites (I) are used as ligands in homogeneous catalysis, such impurities can have an adverse effect on the activity, selectivity and/or stability of the catalyst and/or cause other problems in use, e.g. corrosion problems, or contamination of the product of the catalyzed reaction, e.g. in the form of discoloration.

For the purposes of the invention, the admixing of the organic diphosphite of the general formula (I) dissolved in the first solvent (L1) with a second solvent (L2) is quite generally not limited to a particular order of addition. In principle, the solution of the organic diphosphite (I) in (L1) can be added to (L2) or (L2) can be added to the solution of the organic diphosphite (I) in (L1) or the two liquid media can be combined in another suitable way.

However, in the above-described second variant of the method of the invention, a solution comprising the crude organic diphosphite of the general formula (I) and the first solvent (L1) is added to the second solvent (L2).

The addition of the crude organic diphosphite dissolved in the first solvent (L1) to the second solvent (L2) gives a solid phase enriched in the organic diphosphite and at least one liquid phase enriched in the impurities of the crude organic diphosphite. Solid-liquid phase separation gives a purified diphosphite comprising a lower level of impurities compared to the crude diphosphite.

The impurities can be, for example:
basic compounds, especially the bases used for scavenging hydrogen halide in the process for preparing the organic diphosphite (generally an organic nitrogen-comprising compound, e.g. an amine),
acid salts of the basic compounds,
hydrogen halides and/or salts thereof,
monoxides of the organic diphosphite,
dioxides of the organic diphosphite,
secondary organophosphites as are formed, for example, in the hydrolysis of the phosphochloridite used for introduction of the side wings,
starting materials and intermediates other than the impurities mentioned above from the process for preparing the organic diphosphite,
components other than the impurities mentioned above, e.g. catalysts and additives used in the preparation of the organic diphosphite and/or by-products formed therefrom, etc.,
mixtures of at least two of the abovementioned impurities.

The purified organic diphosphite obtained by the method of the invention preferably has a purity of at least 95%, particularly preferably at least 98%, in particular at least 99.5%.

The purity is for the present purposes the "chemical purity" and refers to the molar proportion of the organic diphosphite obtained by the method of the invention and also the solvates of the organic diphosphite obtained by the method of the invention based on the total solid mixture obtained in the purification. That is to say, solid organic diphosphites which comprise solvent incorporated into the crystal lattice (known as solvate crystals) obtained by the method of the invention are counted as part of the pure compounds.

The organic diphosphite obtained by the method of the invention generally comprises secondary organophosphites in an amount of not more than 1% by weight, particularly preferably not more than 0.5% by weight, in particular not more than 0.2% by weight, based on the total weight of the pure organic diphosphite obtained by the method of the invention, including solvates thereof.

The organic diphosphite obtained by the method of the invention generally comprises nitrogen-comprising compounds in an amount of not more than 20 ppm, particularly preferably not more than 10 ppm, based on the total weight of the pure organic diphosphite, including solvates thereof.

The organic diphosphite obtained by the method of the invention generally comprises halides (especially chloride) in an amount of not more than 20 ppm, particularly preferably not more than 10 ppm, based on the total weight of the pure organic diphosphite obtained by the method of the invention, including solvates thereof.

The organic diphosphite obtained by the method of the invention does not comprise any amounts which can be detected by $^{31}$P-NMR of phosphites D1 and/or D2

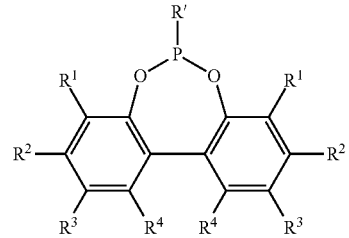

(D1)

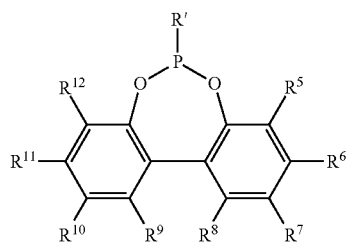

(D2)

where R' is alkoxy, preferably $C_1$-$C_4$-alkoxy, in particular methoxy.

In general, the organic diphosphites purified by the method of the invention can be used without further work-up or purification, e.g. by recrystallization, as ligands in homogenous catalysis.

The first solvent (L1) preferably has a boiling point at 1013 mbar of at least 100° C., particularly preferably at least 110° C.

As first solvent (L1), preference is given to using a solvent or solvent mixture selected from among ($C_1$-$C_4$-alkyl)benzenes, $C_1$-$C_4$-alkyl phenyl ethers, chlorobenzene and mixtures thereof.

($C_1$-$C_4$-alkyl)benzenes suitable as solvent (L1) are, for example, toluene, ethylbenzene, o-, m- or p-xylene, cumene (isopropylbenzene) and mixtures thereof.

($C_1$-$C_4$-alkyl) phenyl ethers suitable as solvent (L1) are, for example, anisole (methyl phenyl ether), ethoxybenzene (phenetole), propoxybenzene, isopropoxybenzene and mixtures thereof.

The first solvent (L1) is particularly preferably selected from among toluene, ethylbenzene, o-, m- or p-xylene, cumene, anisole, chlorobenzene and mixtures thereof.

In particular, toluene is used as first solvent (L1).

As second solvent (L2), use is made according to the invention of a solvent or solvent mixture selected from among linear $C_1$-$C_4$-alkanols, ethylene glycol di($C_1$-$C_4$-alkyl) ethers and mixtures thereof.

The second solvent (L2) is particularly preferably selected from among methanol, ethanol, ethylene glycol dimethyl ether and mixtures thereof.

Surprisingly, no appreciable alcoholysis of the organic diphosphites (I) is observed even when using linear $C_1$-$C_4$-alkanols as second solvent (L2).

In particular, methanol is used as second solvent (L2).

The first solvent (L1) and the second solvent (L2) are preferably completely miscible with one another. If a first solvent (L1) and a second solvent (L2) which are not completely miscible with one another are used, they are preferably used in a ratio which is not in a miscibility gap.

Use of a sufficient amount of the second solvent (L2) makes it possible for the organic diphosphite which is at least partly dissolved in the solvent (L1) to be precipitated essentially completely. The abovementioned solvents (L1) and (L2) result in a liquid mother liqor which comprises the major part of the impurities in dissolved form.

The addition of the solution of the crude organic diphosphite (I) in the first solvent (L1) to the second solvent (L2) can be carried out in a single addition step or in portions. If desired, the addition can also be carried out in the form of a fractional crystallization, with the fractions obtained each being able to be isolated before the further addition of (L2). The weight ratio of first solvent (L1) to second solvent (L2) is advantageously selected so that the organic diphosphite (I) to be purified is precipitated virtually completely after complete addition of the second solvent (L2).

The weight ratio of L1 to L2 is preferably in the range from 1:99 to 95:5, particularly preferably from 2:98 to 90:10, in particular from 5:95 to 80:20.

In a particularly preferred embodiment, toluene is used as solvent (L1) and methanol is used as solvent (L2). The weight ratio of L1 to L2 is then preferably in the range from 1:99 to 75:25, particularly preferably from 1:99 to 50:50. A particularly preferred weight ratio of toluene (L1) to methanol (L2) is in the range from 35:65 to 45:55.

The precipitated organic diphosphite is preferably separated off from the liquid phase and the organic diphosphite which has been separated off is subjected to washing with a liquid washing medium. The organic disphosphite can be subjected to a treatment with a washing medium either once or a plurality of times in succession. Suitable washing media are those in which the organic diphosphites (I) do not dissolve or dissolve only in small amounts and which readily dissolve the impurities in the diphosphites. Preferred washing media are the above-described second solvents (L2). The second solvent (L2) which is also used for the precipitation is preferably used as washing medium. A particularly preferred washing medium is methanol. In a particularly preferred embodiment, the organic diphosphite is firstly subjected to single or multiple washing with methanol and subsequently thereto washing with acetone to displace the methanol.

It has surprisingly been found that addition of a base to the washing medium has an advantageous effect on the stability of the organic diphosphite purified by the method of the invention. In the case of a plurality of washing steps, the base can be added in one or more of the washing steps. This applies, for example, to the washing medium used in the last washing step in the case of a plurality of washing steps. The base is particularly preferably added in all washing steps using methanol. In a preferred embodiment, the organic diphosphite which has been separated off from the liquid phase is therefore firstly subjected to single or multiple washing with basic methanol and to final washing with acetone to displace the methanol and to displace residues of base.

The base is advantageously dissolved in the washing medium. Suitable bases are, for example, alkali metal hydroxides, e.g. NaOH and KOH, and alkali metal alkoxides, e.g. sodium methoxide, potassium methoxide, sodium tert-butoxide, potassium tert-butoxide, sodium tert-pentoxide and potassium tert-pentoxide, etc.

Preference is given to using an alkali metal alkoxide, in particular sodium methoxide, as base.

In a particularly preferred embodiment, methanol to which sodium methoxide has been added as base is used as washing medium.

A base is preferably added to the washing medium in an amount of from 0.01 to 10% by weight, particularly preferably from 0.05 to 5% by weight, based on the total weight of the washing medium.

The use of a base as additive to the washing medium significantly reduces the risk of no longer controllable decomposition of the organic diphosphite on heating, e.g. on drying at temperatures above 150° C.

As regards the configuration of washing with the washing medium, the information given below under step d) is fully incorporated by reference.

The organic diphosphite used for purification is preferably selected from among diphosphite compounds as are described, for example, in EP 0 214 622 A2, U.S. Pat. No. 4,668,651, U.S. Pat. No. 4,769,498, U.S. Pat. No. 5,663,403, U.S. Pat. No. 5,728,861 and U.S. Pat. No. 6,172,267, which are hereby fully incorporated by reference.

The method of the invention is also suitable for purifying organic diphosphites in which one of the phosphorus atoms or both phosphorus atoms are not part of a heterocycle. Such organic diphosphites can, for example, be obtained by reaction of $PCl_3$ with two molar equivalents or four molar equivalents of the appropriate monoalcohols (instead of one molar equivalent or two molar equivalents of the diols forming the side wings) and subsequent reaction with the diol forming the bridging group between the phosphorus atoms. Such diphosphite compounds and their preparation are described, for example, in U.S. Pat. No. 4,748,261, U.S. Pat. No. 4,885,401, U.S. Pat. No. 5,235,113 and U.S. Pat. No. 5,391,801, which are hereby fully incorporated by reference.

In a particularly preferred embodiment, possible compounds are the compounds mentioned in U.S. Pat. No. 4,668, 651, in particular the compounds described in column 9, line 25 to column 16, line 53 and examples 1 to 11 and also ligands A to Q.

In a particularly preferred embodiment, possible compounds are the compounds mentioned in U.S. Pat. No. 4,748, 261, in particular the compounds described in column 14, line 26 to column 62, line 48 and examples 1 to 14 and also ligands 1 to 8.

In a particularly preferred embodiment, possible compounds are the compounds mentioned in U.S. Pat. No. 4,769, 498, in particular the compounds described in column 9, line 27 to column 18, line 14 and examples 1 to 14 and also ligands A to Q.

In a particularly preferred embodiment, possible compounds are the compounds mentioned in U.S. Pat. No. 4,885, 401, in particular the compounds described in column 12, line 43 to column 30 and examples 1 to 14 and also ligands 1 to 8.

In a particularly preferred embodiment, possible compounds are the compounds mentioned in U.S. Pat. No. 5,235, 113, in particular the compounds described in column 7 to column 40, line 11 and examples 1 to 22.

In a particularly preferred embodiment, possible compounds are the compounds mentioned in U.S. Pat. No. 5,391, 801, in particular the compounds described in column 7 to column 40, line 38 and examples 1 to 22.

In a particularly preferred embodiment, possible compounds are the compounds mentioned in U.S. Pat. No. 5,663, 403, in particular the compounds described in column 5, line 23 to column 26, line 33 and examples 1 to 13.

In a particularly preferred embodiment, possible compounds are the compounds mentioned in U.S. Pat. No. 5,728, 861, in particular the compounds described in column 5, line 23 to column 26, line 23 and examples 1 to 13 and also ligands 1 to 11.

In a particularly preferred embodiment, possible compounds are the compounds mentioned in U.S. Pat. No. 6,172, 267, in particular the compounds described in column 11 to column 40, line 48 and examples 1 and 2 and also ligands 1 to 11.

According to the invention, the organic diphosphite is selected from compounds of the general formula (I)

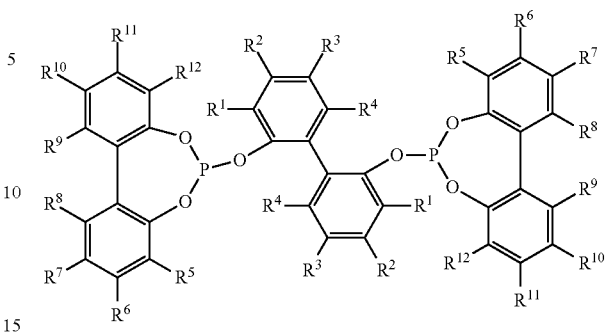

where $R^1$ to $R^{12}$ have the meanings indicated above and in the following.

For the purposes of the invention, halogen is fluorine, chlorine, bromine or iodine, preferably fluorine, chlorine or bromine.

In the following, the expression "$C_1$-$C_{12}$-alkyl" comprises straight-chain and branched $C_1$-$C_{12}$-alkyl groups. Preference is given to unsubstituted straight-chain or branched $C_1$-$C_8$-alkyl groups and very particularly preferably $C_1$-$C_6$-alkyl groups. Examples of $C_1$-$C_{12}$-alkyl groups are, in particular, methyl, ethyl, propyl, isopropyl, n-butyl, isobutyl, sec-butyl, tert-butyl (1,1-dimethylethyl), n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The above explanations in respect of the expression "$C_1$-$C_{12}$-alkyl" also apply to the alkyl groups in $C_1$-$C_{12}$-alkoxy. Preference is given to unsubstituted straight-chain or branched $C_1$-$C_6$-alkoxy groups.

Substituted $C_1$-$C_{12}$-alkyl groups and substituted $C_1$-$C_{12}$-alkoxy groups can, depending on their chain length, have one or more (e.g. 1, 2, 3, 4 or 5) substituents $R^a$. The substituents $R^a$ are preferably selected independently from $C_3$-$C_{12}$-cycloalkyl, $C_3$-$C_{12}$-heterocycloalkyl, $C_6$-$C_{20}$-aryl, fluorine, chlorine, bromine, cyano, formyl, acyl and alkoxycarbonyl.

For the purposes of the present invention, the expression "alkylene" refers to straight-chain or branched alkanediyl groups which preferably have 1 to 6 carbon atoms. These include methylene (—$CH_2$—), ethylene (—$CH_2$—$CH_2$—), n-propylene (—$CH_2$—$CH_2$—$CH_2$—), isopropylene (—$CH_2$—$CH(CH_3)$—), etc.

For the purposes of the present invention, the expression "$C_3$-$C_{12}$-cycloalkyl" comprises monocyclic, bicyclic or tricyclic hydrocarbon radicals having from 3 to 12, in particular from 5 to 12, carbon atoms. They include cyclopropyl, cyclobutyl, cyclopentyl, cyclohexyl, cycloheptyl, cyclooctyl, cyclododecyl, cyclopentadecyl, norbornyl or adamantyl.

For the purposes of the present invention, the expression "$C_3$-$C_{12}$-heterocycloalkyl" comprises nonaromatic, saturated or partially unsaturated cycloaliphatic groups having from 3 to 12, in particular form 5 to 12, carbon atoms. $C_3$-$C_{12}$-heterocycloalkyl groups preferably have from 4 to 8, particularly preferably 5 or 6, ring atoms. In contrast to cycloalkyl groups, 1, 2, 3 or 4 of the ring carbons in heterocycloalkyl groups are replaced by heteroatoms or heteroatom-comprising groups. The heteroatoms or heteroatom-comprising groups are preferably selected from among —O—, —S—, —C(═O)— and —S(═O)$_2$—. Examples of $C_3$-$C_{12}$-heterocycloalkyl groups are tetrahydrothiophenyl, tetrahydrofuranyl, tetrahydropyranyl and dioxanyl.

Substituted $C_3$-$C_{12}$-cycloalkyl groups and substituted $C_3$-$C_{12}$-heterocycloalkyl groups can, depending on their ring size, have one or more (e.g. 1, 2, 3, 4 or 5) substituents Rb. The substituents Rb are preferably selected independently from among $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, fluorine, chlorine, bromine, cyano, formyl, acyl and alkoxycarbonyl. Substituted $C_3$-$C_{12}$-cycloalkyl groups preferably bear one or more, e.g. 1, 2, 3, 4 or 5, $C_1$-$C_6$-alkyl groups. Substituted $C_3$-$C_{12}$-heterocycloalkyl groups preferably bear one or more, e.g. 1, 2, 3, 4 or 5, $C_1$-$C_6$-alkyl groups.

Examples of substituted $C_3$-$C_{12}$-cycloalkyl groups are 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methylcyclooctyl, 2-, 3-, 4- and 5-ethylcyclooctyl, 2-, 3-, 4- and 5-propylcyclooctyl.

For the purposes of the present invention, the expression "$C_6$-$C_{20}$-aryl" comprises monocyclic or polycyclic aromatic hydrocarbon radicals. These have from 6 to 20 ring atoms, particularly preferably from 6 to 14 ring atoms, in particular from 6 to 10 ring atoms. Aryl is preferably $C_6$-$C_{10}$-aryl. Aryl is particularly preferably phenyl, naphthyl, indenyl, fluorenyl, anthracenyl, phenanthrenyl, naphthacenyl, chrysenyl, pyrenyl, coronenyl, perylenyl, etc. In particular, aryl is phenyl or naphthyl.

Substituted $C_6$-$C_{20}$-aryl groups can, depending on their ring size, have one or more (e.g. 1, 2, 3, 4 or 5) substituents $R^c$. The substituents $R^c$ are preferably selected independently from among $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, fluorine, chlorine, bromine, cyano, formyl, acyl and alkoxycarbonyl.

Substituted $C_6$-$C_{20}$-aryl is preferably substituted $C_6$-$C_{10}$-aryl, in particular substituted phenyl or substituted naphthyl. Substituted $C_6$-$C_{20}$-aryl groups preferably bear one or more, e.g. 1, 2, 3, 4 or 5 substituents selected from among $C_1$-$C_6$-alkyl groups, $C_1$-$C_6$-alkoxy groups, chlorine and bromine.

For the purposes of the present invention, the term "acyl" refers to alkanoyl- or aroyl groups which generally have from 2 to 11, preferably from 2 to 8, carbon atoms. They include, for example, acetyl, propanoyl, butanoyl, pentanoyl, hexanoyl, heptanoyl-, 2-ethylhexanoyl, 2-propylheptanoyl, pivaloyl, benzoyl or naphthoyl.

For the purposes of the present invention, carboxylate is preferably a derivative of a carboxylic acid function, in particular a carboxylic ester function or a carboxamide function. Such functions include, for example, the esters with $C_1$-$C_4$-alkanols such as methanol, ethanol, n-propanol, isopropanol, n-butanol, sec-butanol and tert-butanol. Also included are the primary amides and N-alkyl and N,N-dialkyl derivatives thereof.

Fused ring systems can be aromatic, hydroaromatic and cyclic compounds joined by fusion (fused-on). Fused ring systems comprise two, three or more than three rings. Depending on the type of linkage, a distinction is made among fused ring systems between ortho-fusion, i.e. each ring shares an edge or two atoms with each adjacent ring, and peri-fusion in which one carbon atom belongs to more than two rings. Among the fused ring systems, preference is given to ortho-fused ring systems.

In the organic diphosphites of the general formula (I), preference is given to the radicals $R^1$ and $R^3$ each being, independently of one another, $C_1$-$C_4$-alkyl or $C_1$-$C_4$-alkoxy and $R^2$ and $R^4$ each being hydrogen. Greater preference is given to the radicals $R^1$ and $R^3$ being selected independently from among methyl, ethyl, isopropyl, tert-butyl and methoxy and $R^2$ and $R^4$ each being hydrogen.

In the organic diphosphites of the general formula (I), preference is given to the radicals $R^1$, $R^3$ and $R^4$ each being, independently of one another, $C_1$-$C_4$-alkyl or $C_1$-$C_4$-alkoxy and the radicals $R^2$ each being hydrogen. Greater preference is given to $R^1$, $R^3$ and $R^4$ being selected independently from among methyl, ethyl and methoxy and $R^2$ being hydrogen.

In the organic diphosphites of the general formula (I), preference is given to the radicals $R^4$ each being, independently of one another, $C_1$-$C_4$-alkyl or $C_1$-$C_4$-alkoxy and $R^1$, $R^2$ and $R^3$ each being hydrogen. Greater preference is given to the radicals $R^4$ being selected independently from among methyl, ethyl, isopropyl, tert-butyl and methoxy and $R^1$, $R^2$ and $R^3$ each being hydrogen.

In the organic diphosphites of the general formula (I), preference is given to the radicals $R^1$ each being, independently of one another, $C_1$-$C_4$-alkyl or $C_1$-$C_4$-alkoxy and $R^2$, $R^3$ and $R^4$ each being hydrogen. Greater preference is given to the radicals $R^1$ being selected independently from among methyl, ethyl, isopropyl, tert-butyl and methoxy and $R^2$, $R^3$ and $R^4$ each being hydrogen.

In the organic diphosphites of the general formula (I), preference is given to the radicals $R^3$ and $R^4$ together forming a fused benzene ring and $R^1$ and $R^2$ each being hydrogen, i.e. the group of the formula

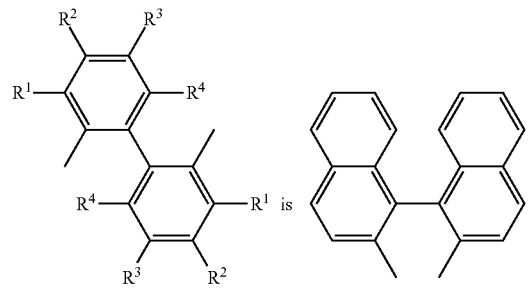

In the organic diphosphites of the general formula (I), the two groups

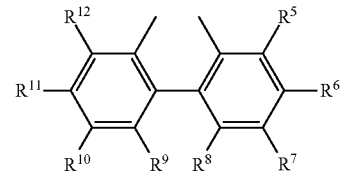

can have identical or different meanings. In a preferred embodiment, both groups have the same meaning.

In the organic diphosphites of the general formula (I), preference is given to the radicals $R^5$ and $R^{12}$ each being, independently of one another, $C_1$-$C_4$-alkyl or $C_1$-$C_4$-alkoxy and $R^6$, $R^7$, $R^8$, $R^9$, $R^{10}$ and $R^{11}$ each being hydrogen. Greater preference is given to $R^5$ and $R^{12}$ being selected independently from among methyl, ethyl, isopropyl, tert-butyl and methoxy and $R^6$, $R^7$, $R^8$, $R^9$, $R^{10}$ and $R^{11}$ each being hydrogen.

In the organic diphosphites of the general formula (I), preference is given to the radicals $R^5$, $R^7$, $R^{10}$ and $R^{12}$ each being, independently of one another, $C_1$-$C_4$-alkyl or $C_1$-$C_4$-alkoxy and $R^6$, $R^8$, $R^9$ and $R^{11}$ each being hydrogen. Greater preference is given to $R^5$, $R^7$, $R^{10}$ and $R^{12}$ being selected independently from among methyl, ethyl, isopropyl, tert-butyl and methoxy and $R^6$, $R^8$, $R^9$ and $R^{11}$ each being hydrogen.

In the organic diphosphites of the general formula (I), preference is given to the radicals $R^5$, $R^7$, $R^8$, $R^9$, $R^{10}$ and $R^{12}$ each being, independently of one another, $C_1$-$C_4$-alkyl or $C_1$-$C_4$-alkoxy and $R^6$ and $R^{11}$ each being hydrogen. Greater preference is given to $R^5$, $R^7$, $R^8$, $R^9$, $R^{10}$ and $R^{12}$ being selected independently from among methyl, ethyl, isopropyl, tert-butyl and methoxy and $R^6$ and $R^{11}$ each being hydrogen.

In the organic diphosphites of the general formula (I), preference is given to the radicals $R^8$ and $R^9$ each being, independently of one another, $C_1$-$C_4$-alkyl or $C_1$-$C_4$-alkoxy and $R^5$, $R^6$, $R^7$, $R^{10}$, $R^{11}$ and $R^{12}$ each being hydrogen, Greater preference is given to $R^8$ and $R^9$ being selected independently from among methyl, ethyl, isopropyl, tert-butyl and methoxy and $R^5$, $R^6$, $R^7$, $R^{10}$, $R^{11}$ and $R^{12}$ each being hydrogen.

In the organic diphosphites of the general formula (I), the radicals $R^5$, $R^6$, $R^7$, $R^8$, $R^9$, $R^{10}$, $R^{11}$ and $R^{12}$ are each preferably hydrogen.

In the compounds of the general formula (I), the group

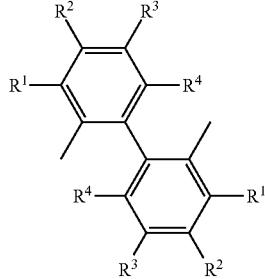

is preferably selected from among 3,3',5,5'-tetramethyl-1,1'-biphenyl-2,2'-diyl, 3,3',5,5'-tetraethyl-1,1'-biphenyl-2,2'-diyl, 3,3',5,5'-tetra-n-propyl-1,1'-biphenyl-2,2'-diyl, 3,3'-dimethyl-5,5'-dichloro-1,1'-biphenyl-2,2'-diyl, 3,3'-diethyl-5,5'-dibromo-1,1'-biphenyl-2,2'-diyl, 3,3'-dimethyl-5,5'-diethyl-1,1'-biphenyl-2,2'-diyl, 3,3'-dimethyl-5,5'-di-n-propyl-1,1'-biphenyl-2,2'-diyl, 3,3',5,5'-tetraisopropyl-1,1'-biphenyl-2,2'-diyl, 3,3',5,5'-tetra-n-butyl-1,1'-biphenyl-2,2'-diyl, 3,3',5,5'-tetraisobutyl-1,1'-biphenyl-2,2'-diyl, 3,3',5,5'-tetra-sec-butyl-1,1'-biphenyl-2,2'-diyl, 3,3',5,5'-tetra(1,1-dimethylethyl)-1,1'-biphenyl-2,2'-diyl, 3,3'-di(1,1-dimethylethyl)-5,5'-di-n-amyl-1,1'-biphenyl-2,2'-diyl, 3,3',5,5'-tetrakis(1,1-dimethylpropyl)-1,1'-biphenyl-2,2'-diyl, 3,3'-di(1,1-dimethylethyl)-5,5'-bis(1,1-dimethylpropyl)-1,1'-biphenyl-2,2'-diyl, 3,3'-di(1,1-dimethylethyl)-5,5'-di-n-hexyl-1,1'-biphenyl-2,2'-diyl, 3,3'-di(1,1-dimethylethyl)-5,5'-di-2-hexyl-1,1'-biphenyl-2,2'-diyl, 3,3'-di(1,1-dimethylethyl)-5,5'-di-3-hexyl-1,1'-biphenyl-2,2'-diyl, 3,3'-di(1,1-dimethylethyl)-5,5'-di-n-heptyl-1,1'-biphenyl-2,2'-diyl, 3,3'-di(1,1-dimethylethyl)-5,5'-di-2-heptyl-1,1'-biphenyl-2,2'-diyl, 3,3'-di(1,1-dimethylethyl)-5,5'-di-3-heptyl-1,1'-biphenyl-2,2'-diyl, 3,3'-di(1,1-dimethylethyl)-5, 5'-di-4-heptyl-1,1'-biphenyl-2,2'-diyl, 3,3'-di(1,1-dimethylethyl)-5,5'-di-n-octyl-1,1'-biphenyl-2,2'-diyl, 3,3'-di(1,1-dimethylethyl)-5,5'-di-2-octyl-1,1'-biphenyl-2,2'-diyl, 5,5'-di-3-octyl-1,1'-biphenyl-2,2'-diyl, 3,3'-di(1,1-dimethylethyl)-5,5'-di-4-octyl-1,1'-biphenyl-2,2'-diyl, 3,3'-di(1,1-dimethylethyl)-5,5'-bis(1,1,3,3-tetramethylbutyl)-1, 1'-biphenyl-2,2'-diyl, 3,3',5,5'-tetrakis(1,1,3,3-tetramethylbutyl)-1,1'-biphenyl-2,2'-diyl, 3,3'-di(1,1-dimethylethyl)-5,5',6,6'-tetramethyl-1,1'-biphenyl-2,2'-diyl, 3,3'-di(1,1-dimethylethyl)-5,5'-diphenyl-1,1'-biphenyl-2,2'-diyl, 3,3'-di(1,1-dimethylethyl)-5,5'-bis(2,4,6,-trimethylphenyl)-1,1'-biphenyl-2,2'-diyl, 3,3'-di(1,1-dimethylethyl)-5,5'-dimethoxy-1,1'-biphenyl-2,2'-diyl, 3,3'-di(1,1-dimethylethyl)-5,5'-diethoxy-1,1'-biphenyl-2,2'-diyl, 3,3'-di(1,1-dimethylethyl)-5,5'-di-n-propoxy-1,1'-biphenyl-2,2'-diyl, 3,3'-di(1,1-dimethylethyl)-5,5'-diisopropoxy-1,1'-biphenyl-2,2'-diyl, 3,3'-di(1,1-dimethylethyl)-5,5'-di-n-butoxy-1,1'-biphenyl-2,2'-diyl, 3,3'-di(1,1-dimethylethyl)-5, 5'-di-sec-butoxy-1,1'-biphenyl-2,2'-diyl, 3,3'-di(1,1-dimethylethyl)-5,5'-diisobutoxy-1,1'-biphenyl-2,2'-diyl, 3,3'-di(1,1-dimethylethyl)-5,5'-di-tert-butoxy-1,1'-biphenyl-2,2'-diyl and 1,1'-binaphthalenyl-2,2'-diyl.

The group

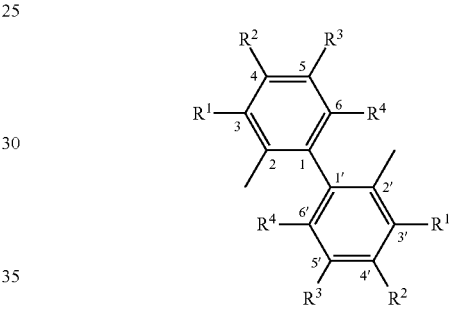

is particularly preferably 3,3',5,5'-tetra(1,1-dimethylethyl)-1, 1'-biphenyl-2,2'-diyl, i.e. particular preference is given to the radicals $R^1$ and $R^3$ in the organic diphosphites of the general formula (I) each being tert-butyl and $R^2$ and $R^4$ each being hydrogen.

In the compounds of the general formula (I), the groups

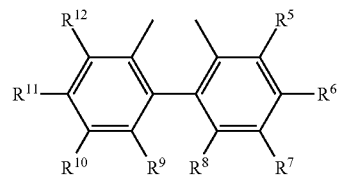

are preferably selected independently from among 1,1'-biphenyl-2,2'-diyl, 5,5'-dimethyl-1,1'-biphenyl-2,2'-diyl, 5,5'-dichloro-1,1'-biphenyl-2,2'-diyl, 5,5'-dibromo-1,1'-biphenyl-2,2'-diyl, 5,5'-diethyl-1,1'-biphenyl-2,2'-diyl, 5,5'-di-n-propyl-1,1'-biphenyl-2,2'-diyl, 5,5'-diisopropyl-1,1'-biphenyl-2,2'-diyl, 5,5'-di-n-butyl-1,1'-biphenyl-2,2'-diyl, 5,5'-di-sec-butyl-1,1'-biphenyl-2,2'-diyl, 5,5'-diisobutyl-1,1'-biphenyl-2,2'-diyl, 5,5'-di(1,1-dimethylethyl)-1,1'-biphenyl-2,2'-diyl, 5,5'-di-n-amyl-1,1'-biphenyl-2,2'-diyl, 5,5'-bis(1,1-dimethylpropyl)-1,1'-biphenyl-2,2'-diyl, 5,5'-bis(1,1-dimethylpropyl)-1,1'-biphenyl-2,2'-diyl, 5,5'-di-n-hexyl-1, 1'-biphenyl-2,2'-diyl, 5,5'-diyl-2-hexyl-1,1'-biphenyl-2,2'-diyl, 5,5'-di-3-hexyl-1,1'-biphenyl-2,2'-diyl, 5,5'-di-n-heptyl-1,1'-biphenyl-2,2'-diyl, 5,5'-di-2-heptyl-1,1'- biphenyl-2,2'-diyl, 5,5'-di-3-heptyl-1,1'-biphenyl-2,2'-diyl, 5,5'-di-4-heptyl-1,1'-biphenyl-2,2'-diyl, 5,5'-di-n-octyl-1,1'-biphenyl-2,2'-diyl, 5,5'-di-2-octyl-1,1'-biphenyl-2,2'-diyl, 5,5'-di-3-octyl-1,1'-biphenyl-2,2'-diyl, 5,5'-di-4-octyl-1,1'-biphenyl-2,2'-diyl, 5,5'-bis(1,1,3,3-tetramethylbutyl)-1,1'-biphenyl-2,2'-diyl, 5,5',6,6'-tetramethyl-1,1'-biphenyl-2,2'-diyl, 5,5'-diphenyl-1,1'-biphenyl-2,2'-diyl, 5,5'-bis(2,4,6,-trimethylphenyl)-1,1'-biphenyl-2,2'-diyl, 5,5'-dimethoxy-1,1'-biphenyl-2,2'-diyl, 5,5'-diethoxy-1,1'-biphenyl-2,2'-diyl, 5,5'-di-n-propoxy-1,1'-biphenyl-2,2'-diyl, 5,5'-diisopropoxy-1,1'-biphenyl-2,2'-diyl, 5,5'-di-n-butoxy-1,1'-biphenyl-2,2'-diyl, 5,5'-di-sec-butoxy-1,1'-biphenyl-2,2'-diyl, 5,5'-diisobutoxy-1,1'-biphenyl-2,2'-diyl, 5,5'-di-tert-butoxy-1,1-biphenyl-2,2'-diyl and 1,1'-binaphthalinyl-2,2'-diyl.

The groups

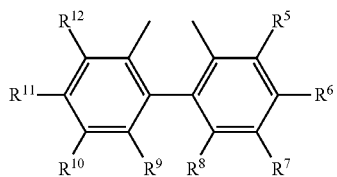

are particularly preferably both 1,1'-biphenyl-2,2'-diyl.

The method of the invention is particularly preferably suitable for purifying the following organic diphosphites:

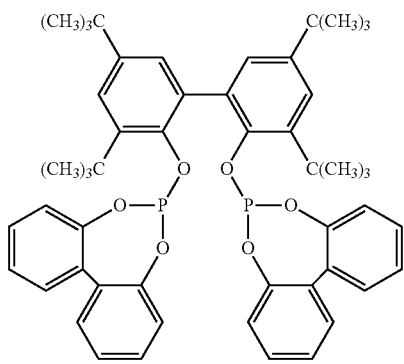

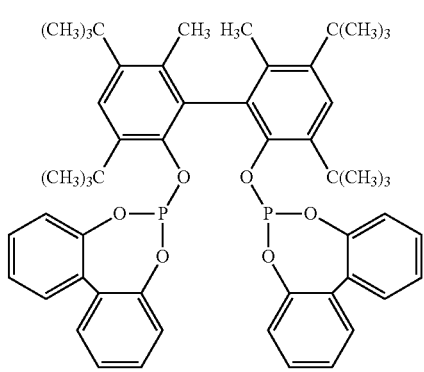

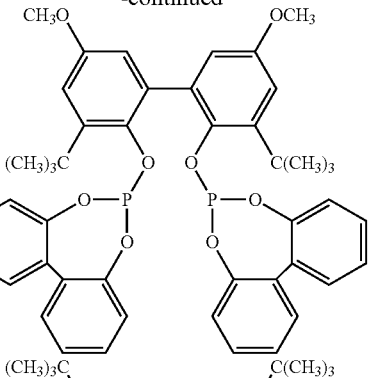

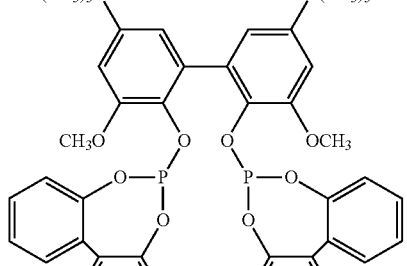

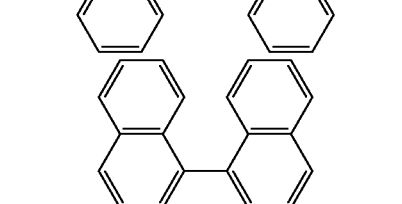

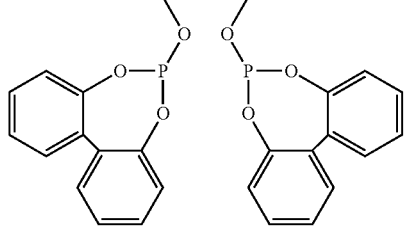

In particular, the organic diphosphite of the formula (I) is 6,6'-[[3,3',5,5'-tetrakis(1,1-dimethylethyl)-[1,1'-biphenyl]-2,2'-diyl]bis(oxy)]bis-dibenzo[d,f][1,3,2]dioxaphosphepin.

Step a)

In a preferred embodiment of the method of the invention, the solution of a crude organic diphosphite provided in step a) is a reaction output from the preparation of organic diphosphites.

The solution of a crude organic diphosphite provided in step a) is preferably a reaction output from a production process as described in EP 0 214 622 A2, U.S. Pat. No. 4,668,651, U.S. Pat. No. 4,748,261, U.S. Pat. No. 4,769,498, U.S. Pat. No. 4,885,401, U.S. Pat. No. 5,235,113, U.S. Pat. No. 5,391,801, U.S. Pat. No. 5,663,403, U.S. Pat. No. 5,728,861, U.S. Pat. No. 6,172,267, WO 2003/062171 and WO 2003/062251.

In a preferred embodiment, the solution of a crude organic diphosphite provided in step a) is a reaction output from a production process as described in WO 2003/062171 and WO 2003/062251.

The solution of a crude organic diphosphite provided in step a) preferably has a solvent selected from among toluene, ethylbenzene, o-, m- or p-xylene, cumene, anisole and mixtures thereof. In particular, a solvent comprising toluene or consisting of toluene is used. Of course, it is also possible to subject a reaction output from the preparation of the organic diphosphites to a solvent exchange in order to provide the solution of a crude organic diphosphite in step a). However, such a procedure is not preferred.

The preparation of the diphosphites used according to the invention for purification may in principle be carried out by means of a sequence of known phosphorus halide-alcohol condensation reactions.

A specific embodiment is a process in which an organic diphosphite (I)

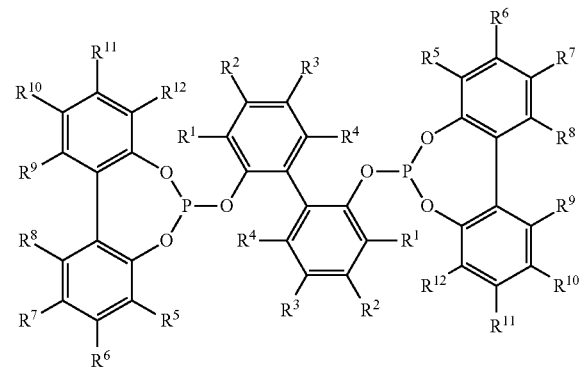

where $R^1$, $R^2$, $R^3$ and $R^4$, $R^5$, $R^6$, $R^7$, $R^8$, $R^9$, $R^{10}$, $R^{11}$ and $R^{12}$ are as defined above, is prepared by i) reacting a diol of the general formula (A1)

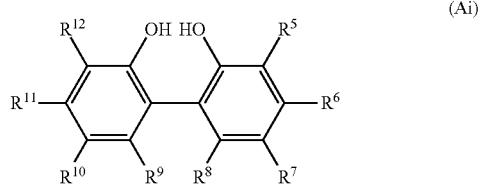

with $PCl_3$ to give a compound (A1)

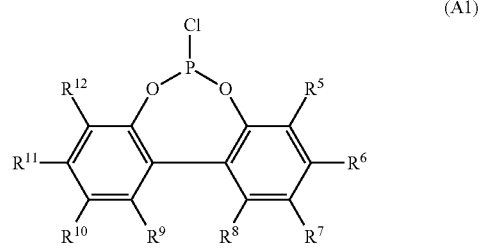

ii) reacting at least one compound (A1) with a diol of the general formula (Aii)

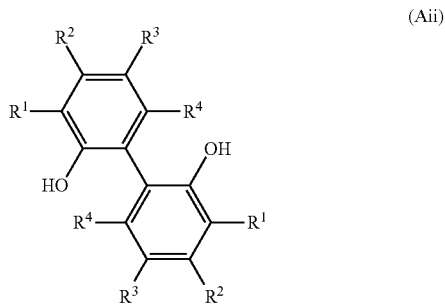

to give the organic diphosphite (I).

As regards suitable and preferred embodiments of the radicals $R^1$, $R^2$, $R^3$, $R^4$, $R^5$, $R^6$, $R^7$, $R^8$, $R^9$, $R^{10}$, $R^{11}$ and $R^{12}$, what has been said above with regard to these radicals is fully incorporated by reference.

As solvent for preparing the organic diphosphites, preference is given to using a solvent or solvent mixture which corresponds to the above-described first solvent (L1).

At least one of the steps i) or ii) is preferably carried out in the presence of a base.

Suitable bases are generally, for example, alkali metal hydroxides, alkaline earth metal hydroxides, alkali metal carbonates, alkaline earth metal carbonates, alkali metal hydrogencarbonates, alkaline earth metal hydrogencarbonates, tertiary amines, basic ion-exchange resins, etc. These include, for example, NaOH, KOH, $Ca(OH)_2$, triethylamine, tripropylamine, tributylamine, etc. Preference is given to tertiary amines and especially triethylamine.

Particular preference is given to a method in which at least one of the steps i) or ii) is carried out in the presence of a base selected from among bases which with the hydrohalic acid formed in the respective reaction step form a salt which is liquid at temperatures at which the reaction product of the respective reaction step is not significantly decomposed during the removal of the liquid salt and the salt forms two immiscible liquid phases with the reaction medium of the respective reaction step.

Suitable bases of this type are described in WO 2003/062171 and WO 2003/062251, which are hereby fully incorporated by reference. Preferred bases of this type are 1-methylimidazole, 1-n-butylimidazole, 2-methylpyridine and 2-ethylpyridine.

In the latter method variant, the major part of the acid salts formed in the condensation reactions from hydrohalic acid and base can advantageously be removed by simple phase separation. Nevertheless, subsequent purification of the reaction output from the purification method of the invention has an advantageous effect on the organic diphosphite (I) obtained. In this way, it is possible to achieve a further significant reduction in the proportion of the abovementioned impurities.

In a preferred embodiment, the reaction in step i) is carried out in the presence of a catalytic amount of an acid salt of a nitrogen base. The acid salt is preferably derived from a nitrogen base selected from among in each case unsubstituted or substituted imidazoles, pyridines, 1H-pyrazoles, 1-pyrazolines, 3-pyrazolines, imidazolines, thiazoles, oxazoles, 1,2, 4-triazoles and 1,2,3-triazoles. The acid salt is particularly preferably derived from an acid selected from among hydrogen chloride, p-toluenesulfonic acid, methanesulfonic acid, 2,4,6-trimethylbenzoic acid and trifluoromethanesulfonic acid. In particular, N-methylimidazolium hydrochloride is used.

Step b1) (=Method Variant 1)

According to the invention, in this method variant the organic diphosphite is partly precipitated by partial removal of the first solvent (L1) and the second solvent (L2) is added to complete the precipitation.

The partial removal of the first solvent (L1) can be effected by conventional methods known to those skilled in the art. These include evaporation under reduced pressure and/or at elevated temperature.

The solvent (L1) is preferably removed to an extent of at least 10% by weight, preferably at least 20% by weight, in particular at least 30% by weight, based on the amount originally used. If toluene is used as first solvent (L1), this is especially removed to an extent of at least 50% by weight, more particularly to an extent of at least 60% by weight, based on the amount originally used.

The solvent (L1) is preferably removed to an extent of not more than 95% by weight, particularly preferably not more than 90% by weight, based on the amount originally used.

The organic diphosphite partly precipitates during removal of the solvent (L1).

In a preferred embodiment, the composition comprising the first solvent (L1) and the partly precipitated organic diphosphite is cooled before the addition of the second solvent (L2) and the temperature is kept low during the addition of the second solvent (L2). The temperature during the addition of the second solvent (L2) is preferably not more than 20° C., particularly preferably not more than 15° C.

Step b2) (=Method Variant 2)

The solution provided in step a) preferably has a temperature in the range from 50 to 180° C., preferably from 60 to 150° C., in particular from 70 to 130° C., on addition to the second solvent in step b2).

The second solvent in step b2) preferably has a temperature in the range from 0 to 50° C., preferably from 15 to 45° C., in particular from 15 to 30° C., when the addition occurs.

In step b2), the temperature difference when the solution provided in step a) is added to the second solvent is preferably at least 20° C., more preferably at least 30° C., in particular at least 40° C.

In a preferred embodiment, the second solvent (L2) is placed in a reaction vessel in step b2) and the solution of the organic diphosphite provided in step a) is fed as feed stream into the space above the initially charged solvent (L2).

This can be achieved using a conventional addition device whose outlet opening ends above the initially charged solvent (L2). The addition can be effected in the form of individual droplets or in the form of a jet. The amount fed in can be regulated by means of a conventional metering device, e.g. a valve, metering pump, etc. If a hot solution of the organic diphosphite is added to the initially charged solvent (L2), the addition device can be fully insulated.

The addition of the solution of the organic diphosphite to the solvent (L2) is advantageously carried out so that it occurs in free fall, i.e. without touching the walls and without touching the stirrer blades, so that lump formation is avoided.

Step c)

According to the invention, the precipitated organic diphosphite is separated off from the liquid phase in step c) according to both the abovementioned method variants.

The separation can be carried out, for example, by filtration or centrifugation. The separation is preferably carried out by filtration. Customary filtration methods are, for example, cake filtration and deep bed filtration (e.g. as described in A. Rushton, A. S. Ward, R. G. Holdich: Solid-Liquid Filtration and Separation Technology, VCH Verlagsgesellschaft, Weinheim 1996, pages 177 ff., K. J. Ives, in A. Rushton (ed.): Mathematical Models and Design Methods in Solid-Liquid Separation, NATO ASI Series E No. 88, Martinus Nijhoff, Dordrecht 1985, pages 90 ff.) and Cross-flow Filtrations (e.g. as described in J. Altmann, S. Ripperger, J. Membrane Sci. 124 (1997), pages 119-128). To accelerate the filtration, it can be carried out under increased pressure on the solids side or reduced pressure on the outflow side. Customary centrifugation methods are described, for example, in G. Hultsch, H. Wilkesmann, "Filtering Centrifuges," in D. B. Purchas, Solid—Liquid Separation, Upland Press, Croydon 1977, pp. 493-559; and H. Trawinski in "Die aquivalente Klarflache von Zentrifugen", Chem. Ztg. 83 (1959), 606-612. Various construction types such as tube centrifuges and basket centrifuges and also pusher centrifuges and invertible filter centrifuges and plate separators can be used.

The liquid phase separated off in step c) can, if desired, be subjected to a work-up. In a preferred embodiment of the method of the invention, the liquid phase is subjected to a separation into a fraction (C1) comprising essentially the first solvent (L1) and the second solvent (L2) and a fraction (C2) comprising essentially the impurities. For this purpose, the first and second solvents (L1 and L2) can, for example, be at least partly separated off from the liquid phase by vaporization. Suitable separation apparatuses are the distillation columns and evaporators customary for this purpose, e.g. falling film evaporators, forced circulation flash evaporators, short path evaporators or thin film evaporators. Owing to the low volatility of most impurities, complicated apparatuses as are used in the separation of mixtures having boiling points close to one another, e.g. complicated column internals, columns having a large number of theoretical plates, etc., can generally be dispensed with. The fraction (C1) comprising the first solvent (L1) and the second solvent (L2) can be subjected to a further separation into a fraction (C1L1) comprising essentially the first solvent (L1) and a fraction (C1L2) comprising essentially the second solvent (L2). Suitable apparatuses for the work-up by distillation comprise distillation columns such as tray columns which can be equipped with bubble caps, sieve plates, sieve trays, packings, random packing elements, valves, side offtakes, etc., evaporators such as thin film evaporators, falling film evaporators, forced circulation evaporators, Sambay evaporators, etc., and combinations thereof.

The fractions (C1L1) and/or (C1L2) can be reused as first solvent (L1) and/or as second solvent (L2) for purifying organic disphosphites by the method of the invention. Here, it is generally not critical if the second solvent (L2) comprises small proportions (e.g. up to about 5% by weight) of the first solvent (L1).

The fraction (C2) comprising essentially the impurities is discharged from the method. It can, for example, be passed to thermal utilization.

The organic diphosphite obtained in step c) of the method of the invention has a sufficient purity for use as ligand in homogeneous catalysis. However, it can be advantageous, especially for use in a continuous catalytic process, for the organic diphosphite separated off in step c) to be subjected to further washing in step b).

Step d)

In a specific embodiment of the method of the invention, the organic diphosphite obtained in step c) is subjected to a further work-up by washing with a liquid washing medium.

Treatment with a liquid washing medium has been found to be advantageous both for the crystalline organic diphosphites obtained according to method variant 1 (steps a), b1) and c)) and for those obtained according to method variant 2 (steps a), b2) and c)). In the case of the organic diphosphites obtained according to method variant 2 (steps a), b2) and c)), no further purification in addition to a single or multiple treatment with a liquid washing medium is necessary.

If the organic diphosphites obtained according to method variant 1 (steps a), b1) and c)) still comprise small amounts of occluded solvents and/or small amounts of impurities, they can be subjected to an additional work-up comprising a recrystallization in step d). A combination of a recrystallization and a treatment with a liquid washing medium is preferred in variant 1).

Suitable washing media are those mentioned above. A particularly preferred washing medium is methanol.

The treatment of the organic diphosphite with a washing medium is preferably carried out at ambient temperature. The treatment of the organic diphosphite with a washing medium is more preferably carried out at a temperature of at least 15° C., particularly preferably at a temperature of from 15 to 20° C. The treatment of the organic diphosphite with a washing medium is preferably carried out at a temperature of not more than 30° C.

To remove the impurities comprised, the organic diphosphite obtained in step c) can be subjected once or a plurality of times in succession to a treatment with a washing medium. For this purpose, the organic diphosphite is brought into intimate contact with the washing medium in a suitable apparatus and the washing medium is subsequently separated off from the organic diphosphite. Suitable apparatuses are, for example, stirred vessels which, if necessary, can be provided with a heating facility and a facility for condensing and recirculating the washing medium. Another suitable apparatus is a suction filter on which the filter cake is washed with the washing medium. The separation of organic diphosphite from the washing medium is carried out, for example, by filtration or centrifugation. To accelerate the filtration, it can be carried out under increased pressure on the solids side or reduced pressure on the outflow side.

As mentioned above, a base is preferably added to the washing medium. In the case of a plurality of washing steps, the base can be added in one or more of the washing steps. This applies, for example, in the case of a plurality of washing steps to the washing medium used in the last washing step. If the organic diphosphite is firstly subjected to single or multiple washing with methanol and subsequent washing with acetone, the base is preferably added in at least one of the washing steps using methanol. The base is particularly preferably added in all washing steps using methanol. In a preferred embodiment, the organic diphosphite obtained in step c) is firstly subjected to single or multiple washing with basic methanol and subsequent washing with acetone to displace the methanol and displace residues of base.

Suitable bases are those mentioned above as additive to the washing medium. An alkali metal alkoxide, in particular sodium methoxide, is preferably used as base.

In a specific embodiment, methanol to which sodium methoxide has been added is used as washing medium.

A base is preferably added to the washing medium in an amount of from 0.01 to 10% by weight, particularly preferably from 0.05 to 1% by weight, in particular from 0.05 to 0.5% by weight, based on the total weight of the second solvent (L2).

The washing medium loaded with impurities can, for example, be worked up by distillation and be reused as washing medium. Impurities which have been separated off are discharged.

The compounds of the general formula (I) obtained by the purification method of the invention are advantageous as ligands for catalysts in continuous processes. Here, the disadvantages associated with an accumulation of the abovementioned impurities, in particular a reduction in the catalyst operating life, can be significantly reduced. The compounds of the general formula (I) obtained by the purification method of the invention also display good flowability. In addition, they display a low tendency to cake and can also be stored over long periods of time. Mechanical comminution before use is advantageously not necessary in many cases.

The compounds of the general formula (I) obtained by the purification method of the invention are advantageous as ligands for transition metal catalysts for hydroformylation, hydrocyanation or hydrogenation.

In general, the metal concentration in the reaction medium is in the range from about 1 to 10 000 ppm. The molar ratio of ligand to transition metal is generally in the range from about 0.5:1 to 1000:1, preferably from 1:1 to 500:1.

A person skilled in the art will select the transition metal as a function of the reaction to be catalyzed. The transition metal is preferably a metal of group 8, 9 or 10 of the Periodic Table of the Elements. The transition metal is particularly preferably selected from among the metals of groups 9 and 10 (i.e. Co, Ni, Rh, Pd, Ir, Pt).

The catalysts used in one of the abovementioned processes can further comprise at least one further ligand which is preferably selected from among carboxylates, acetylacetonate, arylsulfonates, alkylsulfonates, hydride, CO, olefins, dienes, cycloolefins, nitriles, aromatics and heteroaromatics, ethers and monodentate, bidentate and polydentate phosphoramidite and phosphite ligands in addition to the above-described compounds of the formula (I). The further ligands are especially selected from among hydride, CO and olefins, i.e. components which are able to form, together with the diphosphite (I) and the central atom, the active form of the catalyst under hydroformylation conditions.

In a preferred embodiment, the catalysts used according to the invention are prepared in-situ in the reactor used for the reaction. However, if desired, the catalysts can also be prepared separately and be isolated by conventional methods. To prepare the catalysts according to the invention in situ it is possible, for example, to react at least one ligand which has been purified according to the invention, a compound or a complex of a transition metal, optionally at least one further additional ligand and optionally an activator in an inert solvent under the conditions of the reaction to be catalyzed.

Suitable catalyst precursors are very generally transition metals, transition metal compounds and transition metal complexes.

Suitable rhodium compounds or complexes are, for example, rhodium(II) and rhodium(III) salts, e.g. rhodium(II) or rhodium(III) carboxylate, rhodium(II) and rhodium(III) acetate, etc. Rhodium complexes such as biscarbonylrhodium acetylacetonate, acetylacetonatobisethylenerhodium(I), acetylacetonatocyclooctadienylrhodium(I), acetylacetonatonorbornadienylrhodium(I), acetylacetonatocarbonyltriphenylphosphinerhodium(I), etc., are also suitable.

Suitable cobalt compounds for preparing the hydroformylation catalysts are, for example, cobalt(II) sulfate, cobalt(II) carbonate, amine or hydrate complexes thereof, cobalt carboxylates such as cobalt acetate, cobalt ethylhexanoate, cobalt naphthanoate and cobalt caproate. Carbonyl complexes of cobalt, e.g. octacarbonyldicobalt, dodecacarbonyl tetracobalt and hexadecacarbonyl hexacobalt, are also suitable.

The transition metal compounds and complexes mentioned and further suitable transition metal compounds and complexes are known in principle and are adequately described in the literature, or can be prepared by a person skilled in the art using methods analogous to those for the compounds which are already known.

The catalysts according to the invention are preferred for use in hydroformylation. In the case of hydroformylation catalysts, catalytically active species are generally formed from the catalysts or catalyst precursors used in each case under the hydroformylation conditions. For this purpose, an element of group 9 of the Periodic Table of the Elements and in particular rhodium or cobalt is preferably used as metal.

In the hydroformylation and/or the work-up of the catalysts, it is possible to employ measures which increase the catalytic activity and/or avoid decomposition of the catalyst. Such methods are described, for example, in EP 0 590 613, EP 0 865 418, EP 0 874 796, EP 0 874 797, EP 0 876 321, EP 0 876 322, EP 0 904 259, EP 1 019 352 and EP 1 019 353. The teaching of these documents is hereby fully incorporated by reference.

The hydroformylation can be carried out in a suitable solvent which is inert under the respective reaction conditions. Suitable solvents are, for example, the aldehydes formed in the hydroformylation and higher-boiling reaction components, e.g. the products of aldol condensation. Further suitable solvents are aromatics such as toluene and xylenes, hydrocarbons and mixtures of hydrocarbons, esters of aliphatic carboxylic acids with alkanols, for example Texanol®, and esters of aromatic carboxylic acids, e.g. $C_8$-$C_{13}$-dialkyl phthalates.

As regards the preparation and use of hydroformylation catalysts, the teaching of the following documents is incorporated by reference: EP 0 214 622 A2, U.S. Pat. No. 4,668,651, U.S. Pat. No. 4,748,261, U.S. Pat. No. 4,769,498, U.S. Pat. No. 4,885,401, U.S. Pat. No. 5,235,113, U.S. Pat. No. 5,391,801, U.S. Pat. No. 5,663,403, U.S. Pat. No. 5,728,861, U.S. Pat. No. 6,172,267, DE 103 60 771A1, WO 2003/062171 and WO 2003/062251.

Suitable olefin starting materials for the hydroformylation process according to the invention are in principle all compounds which comprise one or more ethylenically unsaturated double bonds. They include olefins having terminal double bonds and those having internal double bonds, straight-chain and branched olefins, cyclic olefins and olefins which have substituents which are essentially inert under the hydroformylation conditions. Preference is given to olefin starting materials comprising olefins having from 2 to 12, particularly preferably from 3 to 8, carbon atoms.

Suitable •-olefins are, for example, ethylene, propene, 1-butene, 1-pentene, 1-hexene, 1-heptene, 1-octene, 1-nonene, 1-decene, 1-undecene, 1-dodecene, etc. Preferred branched internal olefins are $C_4$-$C_{20}$-olefins such as 2-methyl-2-butene, 2-methyl-2-pentene, 3-methyl-2-pentene, internal heptene mixtures, branched, internal octene mixtures, branched, internal nonene mixtures, branched, internal decene mixtures, branched, internal undecene mixtures, branched, internal dodecene mixtures, etc. Further suitable olefins are $C_5$-$C_8$-cycloalkenes such as cyclopentene, cyclohexene, cycloheptene, cyclooctene and derivatives thereof, e.g. $C_1$-$C_{20}$-alkyl derivatives thereof having from 1 to 5 alkyl substituents. Further suitable olefins are vinylaromatics such as styrene, •-methylstyrene, 4-isobutylstyrene, etc. Further suitable olefins are the esters, monoesters and amides of •••-ethylenically unsaturated monocarboxylic and/or dicarboxylic acids, e.g. methyl 3-pentenoate, methyl 4-pentenoate, methyl oleate, methyl acrylate, methyl methacrylate, unsaturated nitriles such as 3-pentenenitrile, 4-pentenenitrile, acrylonitrile, vinyl ethers such as vinyl methyl ether, vinyl ethyl ether, vinyl propyl ether, etc., vinyl chloride, allyl chloride, $C_3$-$C_{20}$-alkenols, -alkenediols and -alkadienols, e.g. allyl alcohol, hex-1-en-4-ol, oct-1-en-4-ol, 2,7-octadienol-1. Further suitable substrates are dienes or polyenes having isolated or conjugated double bonds. These include, for example, 1,3-butadiene, 1,4-pentadiene, 1,5-hexadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, vinylcyclohexene, dicyclopentadiene, 1,5,9-cyclooctatriene and butadiene homopolymers and copolymers.

In a specific embodiment, an industrially available olefin-comprising hydrocarbon mixture is used in the hydroformylation process.

A preferred industrial olefin mixture is the $C_4$ fraction. $C_4$ fractions can be obtained, for example, by fluid catalytic cracking or steam cracking of gas oil or by steam cracking of naphtha. Depending on the composition of the $C_4$ fraction, a distinction is made between the total $C_4$ fraction (crude $C_4$ fraction), the raffinate I obtained after 1,3-butadiene has been separated off and the raffinate II obtained after isobutene has been separated off. Raffinate II is particularly suitable as olefin-comprising hydrocarbon mixture for the hydroformylation.

A particularly preferred industrial olefin mixture is the $C_3$ fraction. Propylene streams suitable as starting material can comprise not only propene but also propane. The propane content is, for example, from 0.5 to 40% by weight, especially from 2 to 30% by weight, of propane.

The reaction conditions of the abovementioned processes are known in principle to those skilled in the art. A person skilled in the art can therefore find suitable reactors and reaction conditions in the literature relevant to the respective process and adapt them routinely. Suitable reaction temperatures are generally in the range from –100 to 500° C., preferably in the range from –80 to 250° C. Suitable reaction pressures are generally in the range from 0.0001 to 600 bar, preferably from 0.5 to 300 bar. The processes can generally be carried out continuously, semicontinuously or batchwise. Preference is given to continuous processes. Suitable reactors for the continuous reaction are known to those skilled in the art and are described, for example, in Ullmanns Enzyklopädie der technischen Chemie, vol. 1, 3rd edition, 1951, p. 743 ff. Suitable pressure-rated reactors are likewise known to those skilled in the art and are described, for example, in Ullmanns Enzyklopädie der technischen Chemie, vol. 1, 3rd edition, 1951, p. 769 ff.

The compounds of the general formula (I) obtained by the purification method of the invention are advantageous as ligands for catalysts for hydrocyanation.

The catalysts used for hydrocyanation also comprise complexes of a metal of transition group VIII, in particular nickel, ruthenium, rhodium, palladium, platinum, preferably nickel, palladium and platinum and very particularly preferably nickel. The metal complexes can be prepared as described above. The same applies to the in-situ preparation of the hydrocyanation catalysts according to the invention. Hydrocyanation processes are described in J. March, Advanced Organic Chemistry, 4th edition, pp. 811-812, which is hereby incorporated by reference.

As regards the preparation and use of hydrocyanation catalysts, U.S. Pat. No. 6,127,567 is fully incorporated by reference.

The organic diphosphites which have been purified by the method of the invention are also advantageous as ligands of a hydrogenation catalyst. The catalysts according to the invention used for hydrogenation preferably comprise at least one metal of group 9 or 10 of the Periodic Table of the Elements, i.e. a metal selected from among Rh, Ir, Ni, Co, Pd and Pt.

The amount of catalyst to be used depends, inter alia, on the respective catalytically active metal and on the form in which it is used and can be determined in each particular case by a person skilled in the art. Thus, for example, an Ni- or Co-comprising hydrogenation catalyst is used in an amount of preferably from 0.1 to 70% by weight, particularly preferably from 0.5 to 20% by weight and in particular from 1 to 10% by weight, based on the weight of the compound to be hydrogenated. The amount of catalyst indicated relates to the amount of active metal, i.e. to the catalytically active component of the catalyst. When noble metal catalysts comprising, for example, rhodium, ruthenium, platinum or palladium are used, amounts which are smaller by a factor of about 10 are used.

The hydrogenation is preferably carried out at a temperature in the range from 0 to 250° C., particularly preferably in the range from 20 to 200° C. and in particular in the range from 50 to 150° C.

The reaction pressure in the hydrogenation reaction is preferably in the range from 1 to 300 bar, particularly preferably in the range from 50 to 250 bar and in particular in the range from 150 to 230 bar.

Both the reaction pressure and the reaction temperature depend, inter alia, on the activity and amount of the hydrogenation catalyst used and can be determined in each particular case by a person skilled in the art.

The hydrogenation can be carried out in a suitable solvent or undiluted in bulk. Suitable solvents are those which are inert under the reaction conditions, i.e. neither react with the starting material or product nor are changed themselves, and can be separated off without problems from the isoalkanes obtained. Suitable solvents include, for example, open-chain and cyclic ethers such as diethyl ether, methyl tert-butyl ether, tetrahydrofuran or 1,4-dioxane and alcohols, in particular $C_1$-$C_3$-alkanols such as methanol, ethanol, n-propanol or isopropanol. Mixtures of the abovementioned solvents are also suitable.

The hydrogen required for the hydrogenation can be used either in pure form or in the form of hydrogen-comprising gas mixtures. However, the latter must not comprise any damaging amounts of catalyst poisons such as sulfur-comprising compounds or CO. Examples of suitable hydrogen-comprising gas mixtures are those from the reforming process. However, hydrogen is preferably used in pure form.

The hydrogenation can be carried out either continuously or batchwise.

The hydrogenation is generally carried out with the compound to be hydrogenated being initially charged, optionally in a solvent. This reaction solution is subsequently preferably admixed with the hydrogenation catalyst before the introduction of hydrogen is then commenced. Depending on the hydrogenation catalyst used, the hydrogenation is carried out at elevated temperature and/or superatmospheric pressure. The reaction under superatmospheric pressure can be carried out using the customary pressure vessels known from the prior art, e.g. autoclaves, stirring autoclaves and pressure reactors. If a superatmospheric pressure of hydrogen is not employed, the customary reaction apparatuses of the prior art which are suitable for atmospheric pressure can be used. Examples are conventional stirred vessels which are preferably provided with evaporative cooling, suitable mixers, introduction devices, optionally heat-exchange elements and inert gas blanketing facilities. In the continuous mode of operation, the hydrogenation can be carried out under atmospheric pressure in reaction vessels, tube reactors, fixed-bed reactors and the like which are customary for this purpose.

The invention is illustrated by the following, nonlimiting examples.

EXAMPLES

Example 1

Synthesis of 6-chlorodibenzo[d,f][1,3,2]dioxaphosphepin using methylimidazolium hydrochloride as catalyst 2,2'-Dihydroxybiphenyl (931.1 g, 5.0 mol) and 1-methylimidazolium hydrochloride (0.9 g, 7.6 mmol) were placed under nitrogen in a 2000 ml double-walled reactor and, after melting of the 2,2'-dihydroxybiphenyl, heated to an internal temperature of 142° C. The introduction of phosphorus trichloride (861.2 g, 6.26 mol) was then commenced while stirring, with it being ensured that the phosphorus trichloride did not get onto the hot reactor wall. The rate of introduction was regulated so that the attached HCl scrubbing tower could absorb all of the HCl formed. A total of three hours were required for the addition of the phosphorus trichloride. After the addition of the phosphorus trichloride, the mixture was stirred at 140° C. for another three hours and a fluid yellow reaction mixture was obtained. The reactor was subsequently evacuated over a period of 40 minutes to a final vacuum of 16 mbar in order to remove the excess phosphorus trichloride. The last residues of phosphorus trichloride were removed by stirring under reduced pressure at 140° C./16 mbar and the mixture was subsequently cooled to 65° C. After admission of nitrogen, toluene (139.2 g) was added and the resulting 90% strength by weight solution (1390 g) of the product was drained into a screw-cap bottle and closed under argon. According to $^{31}$P-NMR, the product had a purity of 98.7%.

Example 2

Synthesis of 6-chlordibenzo[d,f][1,3,2]dioxaphosphepin using N-methylpyrrolidone as catalyst A 600 liter vessel provided with inclined-blade stirrer, condenser, offgas discharge facility via a scrubbing tower and a facility for generating vacuum was charged under nitrogen with 2,2'-dihydroxybiphenyl (88.0 kg, 473 mol) and N-methylpyrrolidone (0.337 kg, 3.4 mol). The mixture was melted by heating to an internal temperature of 140° C. and phosphorus trichloride (88.5 kg, 644 mol) was then introduced at 140° C. over a total period of 7 hours. The slightly endothermic reaction proceeded with vigorous HCl evolution and gentle reflux. After all of the phosphorus trichloride had been added, the mixture was stirred at 140° C. for another 9 hours and was then cooled to an internal temperature of the vessel of 50° C. The vessel was subsequently slowly evacuated at 50° C. to a final pressure of 20 mbar (condenser temperature 5° C.) in order to remove the excess phosphorus trichloride. Excess phosphorus trichloride distilled off during this evacuation. To complete the removal of phosphorus trichloride, the vessel was subsequently heated to an internal temperature of 140° C. and stirred at this temperature and 20 mbar for another three hours. The product obtained was then cooled to 90° C. and used directly for the synthesis in example 3.

Example 3

6,6'-[[3,3',5,5'-Tetrakis(1,1-dimethylethyl)-[1,1'-biphenyl]-2,2'-diyl]bis(oxy)]bisdibenzo[d,f][1,3,2]dioxaphosphepin A solution of 3,3',5,5'-tetra(1,1-dimethylethyl)-1,1'-biphenyl-2,2'-diol (92.7 kg) in a mixture of 1-methylimidazole (40.8 kg) and toluene (313.5 kg) was added to the melt of 6-chlorodibenzo[d,f][1,3,2]dioxaphosphepin (118.4 kg) obtained according to example 2 at 85° C. over a period of 60 minutes while stirring. At the end of the addition, two phases were present and these were stirred at 80° C. for another one hour. The internal temperature was then increased to 90° C., the stirrer was switched off to allow phase separation and the phases were left to separate at 90° C. for 20 minutes. 1-Methylimidazolium hydrochloride (59 kg) was obtained as lower phase and this crystallized out immediately. A $^{31}$P-NMR of the upper phase remaining in the vessel confirmed that it was a solution of 6,6'-[[3,3',5,5'-tetrakis(1,1-dimethylethyl)-[1,1'-biphenyl]-2,2'-diyl]bis(oxy)]bisdibenzo[d,f][1,3,2]dioxaphosphepin in toluene. To carry out purification according to the above-described variant 1, the vessel contents obtained were heated to reflux (113° C.) and stirred under reflux for three hours. Toluene was subsequently distilled off under atmospheric pressure (total 218 kg; the internal temperature in the vessel at the end of the distillation was 124° C.). The contents of the vessel were then cooled at a cooling rate of 15° C./h to 70° C. (stirrer speed: 50 rpm) and then cooled further at 10° C./h to 20° C. Methanol (204 kg) was subsequently introduced at 20° C. over a period of 5 hours and the mixture was stirred at 20° C. for a further 30 minutes (stirrer speed 80 rpm). The contents of the vessel (white suspension) was then drained in equal parts into two stainless steel pressure filters. The further procedure for each pressure filter was then as follows: the mother liqor (toluene/methanol mixture) was then filtered off by pressurization with nitrogen. The filtration proceeded very quickly. To wash the filter cake on each pressure filter, fresh methanol (in each case 135 kg) was introduced into the vessel and was stirred at 18° C. and a stirrer speed of 188 rpm for 10 minutes. The methanol was then in each case poured onto the pressure filter without stirring and filtration was again carried out by pressurization with nitrogen. The filter cake on each pressure filter was subsequently washed another four times with methanol (in each case 95 kg) and subsequently blown dry overnight by means of 2 bar of nitrogen until no more filtrate was obtained. The product on each pressure filter was subsequently dried further at a maximum of 50° C. over the course of 61 hours by means of a stream of nitrogen preheated to 50° C. until the methanol content was less than 0.05%. The product (total 134.2 kg, yield 67.7%, based on 2,2'-dihydroxybiphenyl) was obtained as a white solid.

Chloride content (determined by means of ion chromatography): 13 mg/kg,

Nitrogen content (determined in accordance with ASTM D 5762-02): 37 mg/kg.

Example 4

6,6'-[[3,3',5,5'-Tetrakis(1,1-dimethylethyl)-[1,1'-biphenyl]-2,2'-diyl]bis(oxy)]bisdibenzo[d,f][1,3,2]dioxaphosphepin A 2 l double-walled flask was charged under an inert atmosphere with 6-chlorodibenzo-[d,f][1,3,2]dioxaphosphepin (445.6 g as 90% strength solution in toluene, 1.60 mol) and the solution was heated to 85° C. Furthermore, a 2 l conical flask provided with a magnetic stirrer was charged with 1-methylimidazole (141.0 g, 1.60 mol) and toluene (791.5 g) and 3,3',5,5'-tetra(1,1-dimethylethyl)-1,1'-biphenyl-2,2'-diol (320.5 g, 0.78 mol) was added to the stirred mixture, resulting in formation of a virtually colorless solution. This solution was introduced dropwise under an inert atmosphere into the double-walled flask over a period of 80 minutes by means of a dropping funnel. The brown reaction mixture formed was subsequently maintained at 80° C. for 50 minutes and then heated to 90° C. After stirring for another 10 minutes, the stirrer was stopped. Two phases had formed and these were allowed to separate for 70 minutes. The lower phase (1-methylimidazolium hydrochloride) was then drained as a viscose liquid (182.7 g) via the bottom valve and then crystallized very quickly (mp. about 80° C.). The upper phase was then brought to reflux (115° C.) and stirred for a further 3 hours.

In the meantime, a 4 l double-walled reactor provided with a stirrer was arranged underneath the 2 l double-walled reactor and a thermally insulated Teflon tube was attached to the bottom outlet valve of the 2 l reactor and passed through a ground glass joint into the 4 l reactor. The 4 l reactor was charged under an inert atmosphere with methanol (2000 ml) and this was cooled to 20° C. The stirrer speed was subsequently set to 355 rpm and the solution of the ligand in toluene was allowed to run into the methanol in free fall from the 2 l reactor over a period of 70 minutes in such a way that the stream exiting from the Teflon tube came into contact neither with the wall nor with the shaft or the blade of the stirrer. The product precipitated immediately as a white solid. After the addition of the solution of the ligand was complete, the suspension obtained was stirred for another one hour. The product was subsequently filtered off and the 4 l reactor was rinsed with methanol (1000 ml). The filter cake was stirred up with this methanol and filtered with suction and washed another three times with methanol (in each case 1000 ml) and then sucked dry. Drying of the resulting product overnight at 70° C. and 10 mbar gave 605.3 g (90.1%, based on 6-chlorodibenzo[d,f][1,3,2]dioxaphosphepin) of a colorless, free-flowing powder Chloride (ion chromatography): <1 mg/kg, nitrogen (determined in accordance with ASTM D 5762-02): 2 mg/kg.

The product obtained directly after filtration was the toluene monosolvate of 6,6'-[[3,3',5,5'-tetrakis(1,1-dimethylethyl)-[1,1'-biphenyl]-2,2'-diyl]bis(oxy)]bisdibenzo[d,f][1,3,2]dioxaphosphepin. Depending on the severity of the drying conditions, the toluene monosolvate can be converted into the nonsolvate of I.

The toluene monosolvate and mixtures of these two forms of I in various compositions depending on the drying conditions are free-flowing powders which do not tend to cake even after prolonged storage.

FIG. 1 shows the differential scanning calorimetry (DSC) measurement of the methanol-moist filter cake of I obtained in example 4 which has been sucked dry as far as possible. The DSC measurement was carried out using a Mettler Toledo DSC 822e module (amount of sample: 10 mg, open aluminum crucible, heating rate 10K/min).

Despite the astonishing stability of 6,6'-[[3,3',5,5'-tetrakis(1,1-dimethylethyl)-[1,1'-biphenyl]-2,2'-diyl]bis(oxy)]bisdibenzo[d,f][1,3,2]dioxaphosphepin in methanol which is observed, it was found that the methanol-moist filter cake of the pure product cannot be subjected to an excessively high thermal stress during drying since autocatalytic decomposition in which about 260 J/g of heat are liberated commences at an onset temperature of 157° C. Overall, a final temperature of >400° C. is reached as a result of the exothermic decomposition.

Example 5

Stabilization of 6,6'-[[3,3',5,5'-tetrakis(1,1-dimethylethyl)-[1,1'-biphenyl]-2,2'-diyl]bis(oxy)]bisdibenzo[d,f][1,3,2]dioxaphosphepin by addition of sodium methoxide to the methanol in the precipitation and washing and also the final washing of the filter cake with acetone.

Figure 2:
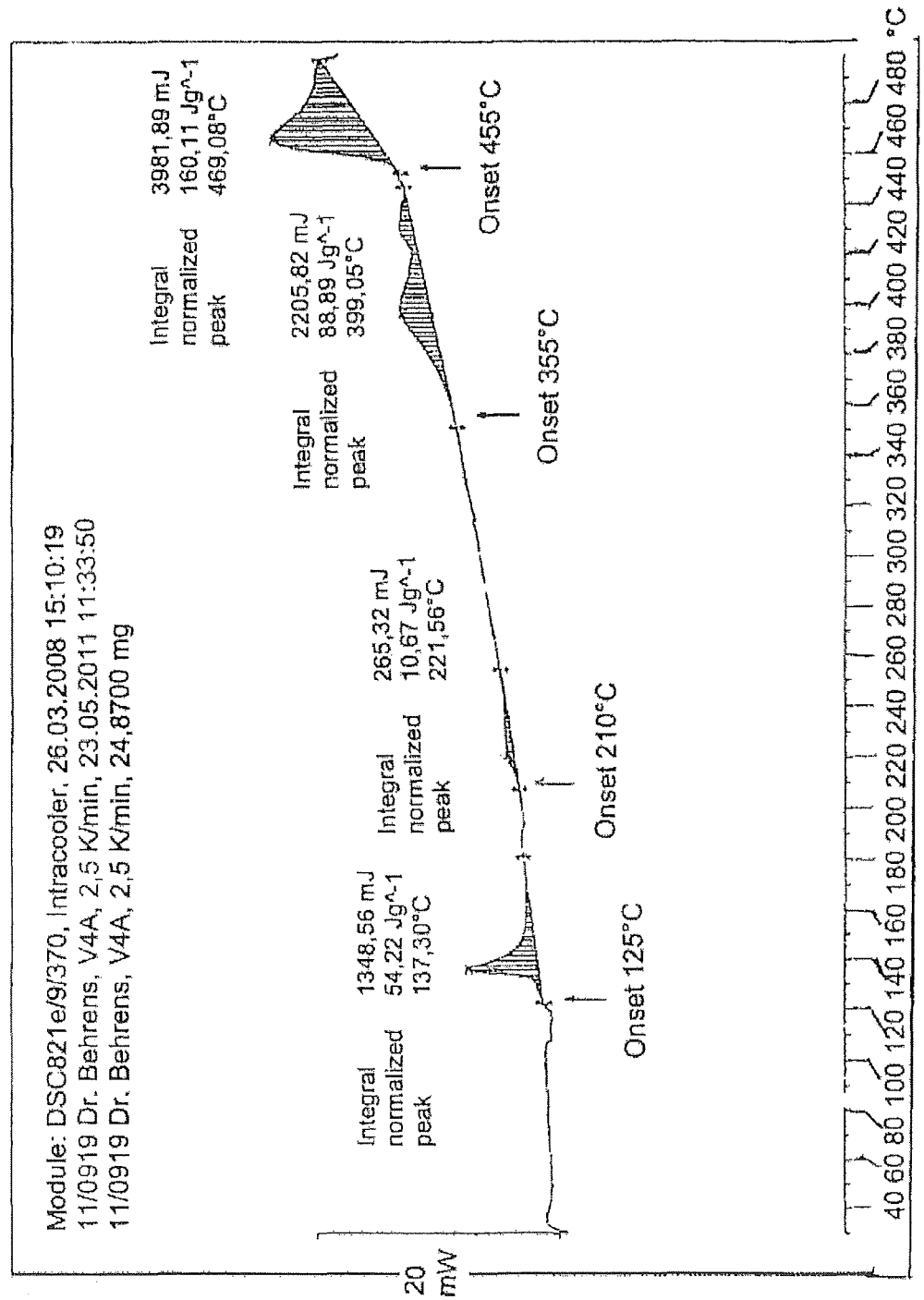
FIG. 2 shows the differential scanning calorimetry (DSC) measurement of the moist crystals of the filter cake obtained in example 5.

The solution of the ligand in toluene was produced in exactly the same way as indicated in example 4. The apparatus for the precipitation of I is the same as that indicated in example 4. To carry out the precipitation, methanol (2000 ml) was placed in the 4 l reactor and sodium methoxide (8.0 g of a 30% strength solution in methanol) was added to this. The stirrer speed was subsequently set to 355 rpm and the solution of the ligand in toluene was allowed to run into the methanol in free fall from the 2 l reactor over a period of 80 minutes in such a way that the stream exiting from the Teflon tube came into contact neither with the wall nor with the shaft or the blade of the stirrer. The product precipitated immediately as a white solid. After the addition of the solution of the ligand was complete, the suspension obtained was stirred for another 110 minutes. The product was subsequently filtered off and the 4 l reactor was rinsed with a mixture of methanol (450 g) and sodium methoxide (2.0 g of a 30% strength solution in methanol). The filter cake was stirred up with this methanol and filtered with suction and washed another three times with a mixture of methanol and sodium methoxide (in each case 450 g of methanol and 2.0 g of a 30% strength sodium methoxide solution in methanol) and then sucked dry. A sample (250 g) of the moist crystals of the filter cake was taken for a DSC measurement and an adiabatic reaction calorimetry measurement. FIG. 2 shows the DSC.

The filter cake was subsequently washed by displacement washing with acetone (500 ml) and good suction was applied. After the product obtained in this way had been dried at 70° C. and 10 mbar for two days, 605.3 g of a colorless, free-flowing powder were obtained.

If sodium methoxide is added to the methanol used in the purification and the subsequent washing steps and an acetone wash is then carried out at the end to displace the NaOMe-comprising methanol from the filter cake, differential calorimetry still shows slight decomposition above an onset temperature of 125° C. but this no longer proceeds autocatalytically. This procedure gives a product whose Na content is very low (<30 ppm) and in which the risk of thermal decomposition is virtually completely ruled out. The heat evolution of about 54 J/g observed brings about heating of about 25° C. which is not sufficient to heat the material further to a hazardous temperature range.

Example 6

Storage tests on 6,6'-[[3,3',5,5'-tetrakis(1,1-dimethylethyl)-[1,1'-biphenyl]-2,2'-diyl]bis(oxy)]bisdibenzo[d,f][1,3,2]dioxaphosphepin which has been purified according to the invention and which has been conventionally recrystallized The product from example 4 is used as product according to the invention.

The product from example 1 which has been purified according to the invention is subjected to a storage test under relatively severe storage conditions with the following parameters:

high relative atmospheric humidity: 95%
high temperature: 40° C.
water vapor-permeable packaging: Mini-Big Bags made of woven PP fabric with PE inliner (material thickness 125·m), dimensions: 350×350×500 mm, volume about 60 liters
high loading (such as three Mini-Big Bags above one another): 6.0 kPa The experiments were carried out over two and four weeks.

The product is for this purpose packed in the above-described Mini-Big Bags and, under the indicated conditions in a controlled-atmosphere cabinet, subjected to the appropriate load by means of weights. After the period of time indicated, the Mini-Big Bags are removed from storage and cut open. Penetration tests are carried out on the surface by means of a penetrometer (PCE Inst. Deutschland GmbH) in order to determine the penetration force.

a) Storage time two weeks:
   slight clod formation on the surface
   some lumps in the core, remainder of the product is very free-flowing
   lumps disintegrate again under a very small mechanical load
   results of penetrometer test: (average of two samples at a different penetration depth with five measurements for each) 6 mm: 0.01N, 12 mm: 0.3 N
b) Storage time four weeks:
   product is loose and free-flowing
   no caking
   no too few lumps having a very low strength
   slight consolidation at the edge of the bag and especially in the corners
   results of penetrometer test: (average of two samples with five measurements for each) 6 mm: 0.0 N, 12 mm: 0.1N The product according to the invention precipitated from methanol as per example 4 is free-flowing and not at all caked even after four weeks. The highest penetration forces were measured after two weeks with a value of 0.3 N.

The invention claimed is:

1. A method of purifying an organic diphosphite of general formula (I)

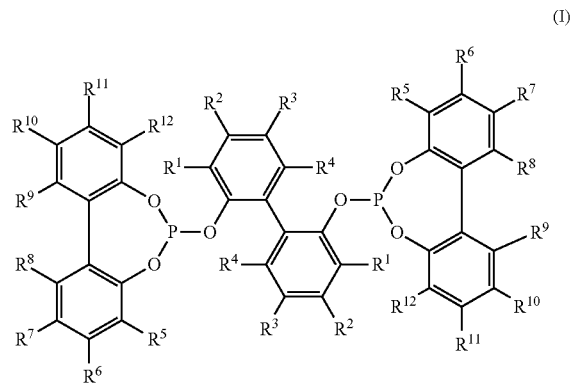

wherein
$R^1$, $R^2$, $R^3$ and $R^4$ are each, independently of one another, hydrogen, unsubstituted straight-chain or branched $C_1$-$C_6$-alkyl, unsubstituted straight-chain or branched $C_1$-$C_6$-alkoxy, $C_6$-$C_{10}$-aryl, chlorine, formyl, acyl or ($C_1$-$C_6$-alkoxy)carbonyl, wherein two adjacent radicals R¹ to R⁴ together with the carbon atoms of the benzene ring to which they are bound optionally define a fused ring system with a further benzene ring, R⁵, R⁶, R⁷, R⁸, R⁹, R¹¹, and R¹² are each, independently of one another, hydrogen, unsubstituted straight-chain or branched $C_1$-$C_6$-alkyl, unsubstituted straight-chain or branched $C_1$-$C_6$-alkoxy, $C_6$-$C_{10}$-aryl, chlorine, formyl, acyl or ($C_1$-$C_6$-alkoxy)carbonyl, where two adjacent radicals R⁵ to R¹² together with the carbon atoms of the benzene ring to which they are bound optionally define a fused ring system with a further benzene ring, the method comprising;

providing a crude organic diphosphite of general formula (I) that is at least partly dissolved in a first solvent (L1), wherein (L1) is selected from the group consisting of alkylbenzenes, aryl alkyl ethers, chlorobenzene, and mixtures thereof, precipitating by admixing with a second solvent (L2) selected from the group consisting of linear $C_1$-$C_4$-alkanols, ethylene glycol di($C_1$-$C_4$-alkyl) ethers, and mixtures thereof, and separating off the precipitated organic diphosphite.

2. The method of claim 1, wherein the precipitated organic diphosphite is subjected to washing with a liquid washing medium.

3. The method of claim 1, wherein the
providing the crude organic diphosphite of general formula (I) and (L1), includes
b1) partly crystallizing out the organic diphosphite by distilling off part of (L1) and, to complete the crystallization, adding the second solvent (L2).

4. The method of claim 1, wherein the
providing the crude organic diphosphite of the general formula (I) and (L1), includes
b2) adding the solution provided in of step a) to the second solvent (L2), with the organic diphosphite at least partly precipitating.

5. The method of claim 1, wherein (L1) is selected from the group consisting of toluene, ethylbenzene, o-xylene, m-xylene, or p-xylene, anisole, ethoxybenzene, propoxybenzene, isopropoxybenzene, chlorobenzene, and mixtures thereof.

6. The method of claim 1, wherein (L1) is toluene.

7. The method of claim 6, wherein (L2) is methanol, ethanol, ethylene glycol dimethyl ether, or mixtures thereof.

8. The method of claim 6, wherein (L2) is methanol.

9. The method of claim 1, wherein the group in general formula (I) is selected from the group consisting of 3,3',5,5'-tetramethyl-1,1'-biphenyl-2,2'-diyl, 3,3',5,5'-tetraethyl-1,1'-biphenyl-2,2'-diyl, 3,3',5,5'-tetra-n-propyl-1,1'-biphenyl-2,2'-diyl, 3,3'-dimethyl-5,5'-dichloro-1,1'-biphenyl-2,2''-diyl, 3,3'-diethyl-5,5'-dibromo-1,1'-biphenyl-2,2'-diyl, 3,3'-dimethyl-5,5'-diethyl-1,1'-biphenyl-2,2'-diyl, 3,3'-dimethyl-5,5'-di-n-propyl-1,1'-biphenyl-2,2'-diyl, 3,3',5,5'-tetraisopropyl-1,1'-biphenyl-2,2'-diyl, 3,3',5,5'-tetra-n-butyl-1,1'-biphenyl-2,2'-diyl, 3,3',5,5'-tetraisobutyl-1,1'-biphenyl-2,2'-diyl, 3,3',5,5'-tetra-sec-butyl-1,1'-biphenyl-2,2'-diyl, 3,3',5,5'-tetra(1,1-dimethylethyl)-1,1'-biphenyl-2,2'-diyl, 3,3'-di(1,1-dimethylethyl)-5,5'-di-n-amyl-1,1'-biphenyl-2,2'-diyl, 3,3',5,5'-tetrakis(1,1-dimethylpropyl)-1,1'-biphenyl-2,2'-diyl, 3,3'-di(1,1-dimethylethyl)-5,5'-bis(1,1-dimethylpropyl)-1,1'-biphenyl-2,2'-diyl, 3,3'-di(1,1-dimethylethyl)-5,5'-di-n-hexyl-1,1'-biphenyl-2,2'-diyl, 3,3'-di(1,1-dimethylethyl)-5,5'-di-2-hexyl-1,1'-biphenyl-2,2'-diyl, 3,3'-di(1,1-dimethylethyl)-5,5'-di-3-hexyl-1,1'-biphenyl-2,2'-diyl, 3,3'-di(1,1-dimethylethyl)-5,5'-di-n-heptyl-1,1'-biphenyl-2,2'-diyl, 3,3'-di(1,1-dimethylethyl)-5,5'-di-2-heptyl-1,1'-biphenyl-2,2'-diyl, 3,3'-di(1,1-dimethylethyl)-5,5'-di-3-heptyl-1,1'-biphenyl-2,2'-diyl, 3,3'-di(1,1-dimethylethyl)-5,5'-di-4-heptyl-1,1'-biphenyl-2,2'-diyl, 3,3'-di(1,1-dimethylethyl)-5,5'-di-n-octyl-1,1'-biphenyl-2,2'-diyl, 3,3'-di(1,1-dimethylethyl)-5,5'-di-2-octyl-1,1'-biphenyl-2,2'-diyl, 5,5'-di-3-octyl-1,1'-biphenyl-2,2'-diyl, 3,3'-di(1,1-dimethylethyl)-5,5'-di-4-octyl-1,1'-biphenyl-2,2'-diyl, 3,3'-di(1,1-dimethylethyl)-5,5'-bis(1,1,3,3-tetramethylbutyl)-1,1'-biphenyl-2,2'-diyl, 3,3',5,5'-tetrakis(1,1,3,3-tetramethylbutyl)-1,1'-biphenyl-2,2'-diyl, 3,3'-di(1,1-dimethylethyl)-5,5',6,6'-tetramethyl-1,1'-biphenyl-2,2'-diyl, 3,3'-di(1,1-dimethylethyl)-5,5'-diphenyl-1,1'-biphenyl-2,2'-diyl, 3,3'-di(1,1-dimethylethyl)-5,5'-bis(2,4,6,-trimethylphenyl)-1,1'-biphenyl-2,2'-diyl, 3,3'-di(1,1-dimethylethyl)-5,5'-dimethoxy-1,1'-biphenyl-2,2'-diyl, 3,3'-di(1,1-dimethylethyl)-5,5'-diethoxy-1,1'-biphenyl-2,2'-diyl, 3,3'-di(1,1-dimethylethyl)-5,5'-di-n-propoxy-1,1'-biphenyl-2,2'-diyl, 3,3'-di(1,1-dimethylethyl)-5,5'-diisopropoxy-1,1'-biphenyl-2,2'-diyl, 3,3'-di(1,1-dimethylethyl)-5,5'-di-n-butoxy-1,1'-biphenyl-2,2'-diyl, 3,3'-di(1,1-dimethylethyl)-5,5'-di-sec-butoxy-1,1'-biphenyl-2,2'-diyl, 3,3'-di(1,1-dimethylethyl)-5,5'-diisobutoxy-1,1'-biphenyl-2,2'-diyl, 3,3'-di(1,1-dimethylethyl)-5,5'-di-tert-butoxy-1,1'-biphenyl-2,2'-diyl, and 1,1'-binaphthalenyl-2,2'-diyl.

10. The method of claim 1, wherein the group in general formula (I) is 3,3',5,5'-tetra-(1,1-dimethylethyl)-1,1'-biphenyl-2,2'-diyl.

11. The method of claim 1, wherein the organic diphosphite of general formula (I) is 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepin.

12. The method of claim 3, wherein the crude solution in step a) is a reaction output from a preparation of the organic diphosphite.

13. The method of claim 12, wherein the preparation of the organic diphosphite is carried out in the presence of (L1).

14. The method of claim 13, wherein the preparation of organic diphosphite is carried out in the presence of a base selected from bases which forms a salt with a hydrohalic acid formed in the preparation of the organic diphosphite, the salt is liquid at temperatures at which the organic diphosphite is not significantly decomposed during removal of the liquid salt, and the salt forms a liquid phase that is immiscible with the reaction medium of the preparation of the organic diphosphite.

15. The method of claim 14, wherein the base is selected from among 1-methylimidazole, 1-n-butylimidazole, 2-methylpyridine and 2-ethylpyridine.

16. The method of claim 4, wherein, in step b2), the solution provided in step a) has a temperature in the range from 50 to 180° C., on addition to the second solvent.

17. The method of claim 4, wherein (L2) in step b2) has a temperature in the range from 0 to 50° C., when the addition occurs.

18. The method of claim 4, wherein, in step b2), the temperature difference when the solution provided in step a) is added to (L2) is at least 20° C.

19. The method of claim 4, wherein in step b2) the solution of step a) is added as a feed stream into a space above an initially charged (L2).

20. The method of claim 2, wherein the washed precipitated organic diphosphite is subjected to a single washing or multiple washings in succession with methanol, and to a subsequent washing with acetone.

21. The method of claim 2, wherein a base is added to the washing medium or, in the case of a plurality of washing steps, to at least one of the washing media.

22. The method of claim 21, wherein the base is an alkali metal hydroxide or alkali metal alkoxide.

23. The method of claim 21, wherein the base is sodium methoxide.

24. The method of claim 1, wherein the purified organic diphosphite of general formula (I) has a halide content of not more than 20 ppm.

25. The method of claim 4, wherein the crude solution provided in step a) is a reaction output from the preparation of the organic diphosphite.

26. The method of claim 25, wherein the preparation of the organic diphosphite is carried out in the presence of (L1).

27. The method of claim 1, wherein the organic diphosphite is 6'-[[3,3',5,5'-tetrakis(1,1-dimethylethyl)-[1,1'-biphenyl]-2,2'-diyl]bis(oxy)]bis-dibenzo[d,f][1,3,2]dioxaphosphepin.

28. A method of purifying an organic diphosphite of general formula (I)

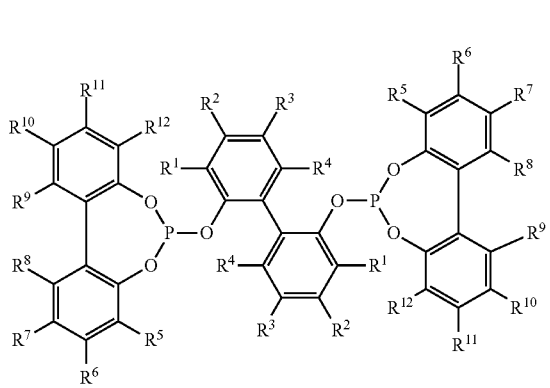

wherein $R^1$, $R^2$, $R^3$ and $R^4$ are each, independently of one another, hydrogen, unsubstituted straight-chain or branched $C_1$-$C_6$-alkyl, unsubstituted straight-chain or branched $C_1$-$C_6$-alkoxy, $C_6$-$C_{10}$-aryl, chlorine, formyl, acyl or ($C_1$-$C_6$-alkoxy)carbonyl, wherein two adjacent radicals $R^1$ to $R^4$ together with the carbon atoms of the benzene ring to which they are bound optionally define a fused ring system with a further benzene ring, $R^5$, $R^6$, $R^7$, $R^8$, $R^9$, $R^{10}$, $R^{11}$ and $R^{12}$ are each, independently of one another, hydrogen, unsubstituted straight-chain or branched $C_1$-$C_6$-alkyl, unsubstituted straight-chain or branched $C_1$-$C_6$-alkoxy, $C_6$-$C_{10}$-aryl, chlorine, formyl, acyl or ($C_1$-$C_6$-alkoxy)carbonyl, where two adjacent radicals $R^5$ to $R^{12}$ together with the carbon atoms of the benzene ring to which they are bound optionally define a fused ring system with a further benzene ring, the method comprising;

providing a crude organic diphosphite of general formula (I) that is at least partly dissolved in a first solvent (L1), wherein (L1) is selected from the group consisting of alkylbenzenes, aryl alkyl ethers, chlorobenzene, and mixtures thereof, crystallizing the organic diphosphite of general formula (I) by admixing with a second solvent (L2) selected from the group consisting of linear $C_1$-$C_4$-alkanols, ethylene glycol di($C_1$-$C_4$-alkyl) ethers, and mixtures thereof, separating the crystallized organic diphosphite from the first solvent (L1) and the second solvent (L2), and washing the separated organic diphosphite with one or a plurality of washing steps, and at least one wash step includes the addition of a base to a wash medium.

29. The method of claim 28, wherein the crude organic diphosphite of general formula (I) is obtained from a preparation of the organic diphosphite in the presence of the first solvent, and the at least partly dissolving includes partly crystallizing out the organic diphosphite by distilling off part of the first solvent, and to complete the crystallization, adding the second solvent (L2).

30. The method of claim 29, wherein the preparation of the organic diphosphite is carried out in the presence of a base selected from the group consisting of 1-methylimidazole, 1-n-butylimidazole, 2-methylpyridine and 2-ethylpyridine.

31. The method of claim 28, wherein the washing the separated organic diphosphite includes a final wash step with acetone.

32. The method of claim 28, wherein the base is an alkali metal hydroxide or an alkali metal alkoxide.

33. The method of claim 32, wherein the second solvent (L2) is a linear $C_1$-$C_4$ alkanol.

34. The method of claim 28, wherein the purified organic diphosphite of general formula (I) has a halide content of not more than 20 ppm.

35. A method of purifying an organic diphosphite of general formula (I)

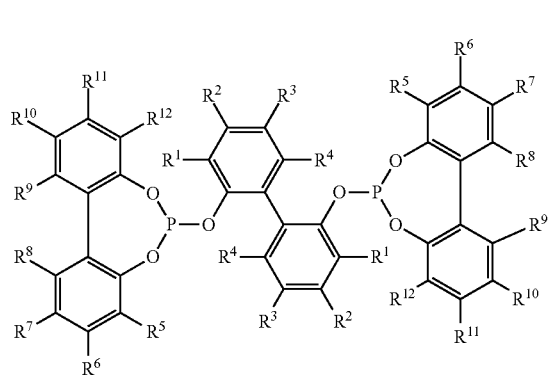

wherein
$R^1$, $R^2$, $R^3$ and $R^4$ are each, independently of one another, hydrogen, unsubstituted straight-chain or branched $C_1$-$C_6$-alkyl, unsubstituted straight-chain or branched $C_1$-$C_6$-alkoxy, $C_6$-$C_{10}$-aryl, chlorine, formyl, acyl or ($C_1$-$C_6$-alkoxy)carbonyl,
wherein two adjacent radicals $R^1$ to $R^4$ together with the carbon atoms of the benzene ring to which they are bound optionally define a fused ring system with a further benzene ring,
$R^5$, $R^6$, $R^7$, $R^8$, $R^9$, $R^{10}$, $R^{11}$ and $R^{12}$ are each, independently of one another, hydrogen, unsubstituted straight-chain or branched $C_1$-$C_6$-alkyl, unsubstituted straight-chain or branched $C_1$-$C_6$-alkoxy, $C_6$-$C_{10}$-aryl, chlorine, formyl, acyl or ($C_1$-$C_6$-alkoxy)carbonyl,
where two adjacent radicals $R^5$ to $R^{12}$ together with the carbon atoms of the benzene ring to which they are bound optionally define a fused ring system with a further benzene ring,
the method comprising;
providing a crude organic diphosphite of general formula (I) that is at least partly dissolved in a first solvent (L1), wherein (L1) is selected from the group consisting of alkylbenzenes, aryl alkyl ethers, chlorobenzene, and mixtures thereof,
crystallizing the organic diphosphite of general formula (I) by admixing with a second solvent (L2) selected from a linear $C_1$-$C_4$-alkanols,
separating the crystallized organic diphosphite from the first solvent (L1) and the second solvent (L2),
wherein the separated organic diphosphite of general formula (I) has a halide content of not more than 20 ppm.

36. The method of claim 35, wherein the separated organic diphosphite of general formula (I) has a halide content of not more than 10 ppm.

37. The method of claim 36, wherein the separated organic diphosphite of general formula (I) has a nitrogen content of not more than 20 ppm.

38. The method of claim 36, wherein the separated organic diphosphite of general formula (I) has a secondary organophosphite content of not more than 0.2% by weight.

39. The method of claim 1, wherein the precipitated organic diphosphite is crystalline.

40. The method of claim 1, wherein the crude organic diphosphite of general formula (I) is a reaction output from a preparation of the organic diphosphite that is carried out in the first solvent (L1).

41. The method of claim 28, wherein the crude organic diphosphite of general formula (I) is a reaction output from a preparation of the organic diphosphite that is carried out in the first solvent (L1).

42. The method of claim 35, wherein the crude organic diphosphite of general formula (I) is a reaction output from a preparation of the organic diphosphite that is carried out in the first solvent (L1).

* * * * *